United States Patent
Quaedflieg et al.

(10) Patent No.: US 7,595,408 B2
(45) Date of Patent: Sep. 29, 2009

(54) METHODS FOR THE PREPARATION OF (3R,3AS,6AR) HEXAHYDRO-FURO[2,3-B]FURAN-3-OL

(75) Inventors: Peter Jan Leonard Mario Quaedflieg, Waalre (NL); Bart Rudolf Romanie Kesteleyn, Berlare (BE); Robert Jan Vijn, Venlo (NL); Constantinus Simon Maria Liebregts, Helmond (NL); Jacob Hermanus Matheus Hero Kooistra, Haren (NL); Franciscus Alphons Marie Lommen, Horst (NL)

(73) Assignee: Tibotec Pharmaceuticals, Ltd., Little Island, Co. Cork (IE)

( * ) Notice: Subject to any disclaimer, the term of this patent is extended or adjusted under 35 U.S.C. 154(b) by 36 days.

(21) Appl. No.: 10/599,497

(22) PCT Filed: Mar. 31, 2005

(86) PCT No.: PCT/EP2005/051452

§ 371 (c)(1),
(2), (4) Date: Sep. 29, 2006

(87) PCT Pub. No.: WO2005/095410

PCT Pub. Date: Oct. 13, 2005

(65) Prior Publication Data

US 2007/0208184 A1 Sep. 6, 2007

(30) Foreign Application Priority Data

Mar. 31, 2004 (EP) .................................. 04101336

(51) Int. Cl.
*C07D 307/93* (2006.01)
*C07D 493/00* (2006.01)
(52) U.S. Cl. .................. 549/311; 549/302; 549/464
(58) Field of Classification Search .................. 549/311, 549/302, 464
See application file for complete search history.

(56) References Cited

U.S. PATENT DOCUMENTS 6,127,372 A  10/2000  Tung et al.
7,126,015 B2 * 10/2006 Kesteleyn et al. ........... 549/464

FOREIGN PATENT DOCUMENTS

EP   715618 B1   6/1996
WO   1995024385 A2   9/1995
WO   1999065870 A2   12/1999
WO   1999067417 A2   12/1999
WO   2000047551 A2   8/2000
WO   1999067417 A3   9/2000
WO   2000076961 A1   12/2000
WO   1999065870 A3   3/2001
WO   2001025240 A1   4/2001
WO   2000047551 A3   8/2001
WO   2003022853 A1   3/2003

OTHER PUBLICATIONS

Ghosh, et al "Potent HIV Protease Inhibitors Incorporating High-Affinity P2-Ligands and (R-Hydroxyethylamino) Sulfonamide Isostere", Bioorganic & Medicinal Chemistry Letters, Oxford GB, vol. 8, No. 6, Mar. 17, (1998) pp. 687-690.
Ghosh et al., "Nonpeptidal P2 Ligands for HIV protease Inhibitors; Structure Based Design, Synthesis, and Biological Evaluation "J. Med. Chem. (1996) vol. 39, pp. 3278-3290.
Pezeck et al., "A New Route to Perhydro and Tetrahydro Furo-2, 3b Furans Via Radical Cyclisation", Tetrahedron Letters, (1986) vol. 27, No. 32, pp. 3715-3718.
Uchiyama et al., "Stereoselevtive synthesis of optically active perhydrofurol [2,3-b] furan derivatives", Tetrahedron Letters, (2001), vol. 42, pp. 4653-4656.
C. Hubschwerlen, "A convenient Syntesis of L-(s) Glyceraldehyde Acetonide form L-Ascorbiic Acid", Synthesis (1986) pp. 962-964.
C .R. Schmid et al., "Synthesis of 2,3 O lsopropylidene glyceraldehyde High Chemical and Optical Purity: Observation on the Development of a Practical Bulk Process", J. Org. Chem. (1991), vol. 56, pp. 4056-4058.
Krief et al., "Diastereoselective Synthesis of Dimethyl Cycloropane-1, 1-Dicarboxylates from a y-Alkosy Alkylidene Malonate and Sulfer and Phosphorus Ylides", Tetrahedron Lett. 1998, 39, 1437-1440.
N. Kornblum "The Synthesis of Aliphatic and Nitro Compounds", Organic reactions, (1962), vol. 12, 101.
H.W. Pinnick, Organic Reactions (1990), vol. 38, pp. 655-792.

* cited by examiner

*Primary Examiner*—D. Margaret Seaman
*Assistant Examiner*—Nizal S Chandrakumar

(57) ABSTRACT

The present invention relates to methods for the preparation of diastereomerically pure (3R,3aS,6aR) hexahydro-furo[2,3-b]furan-3-ol as well as a novel intermediate, (3aR,4S,6aS) 4-methoxy-tetrahydro-furo[3,4-b]furan-2-one for use in said methods. More in particular the invention relates to a stereoselective method for the preparation of diastereomerically pure (3R,3aS,6aR) hexahydro-furo[2,3-b]furan-3-ol, as well as methods for the crystallization of (3aR,4S,6aS) 4-methoxy-tetrahydro-furo[3,4-b]furan-2-one and for the epimerization of (3aR,4R,6aS) 4-methoxy-tetrahydro-furo[3,4-b]-furan-2-one to (3aR,4S,6aS) 4-methoxy-tetrahydro-furo[3,4-b]furan-2-one.

20 Claims, No Drawings

METHODS FOR THE PREPARATION OF (3R,3AS,6AR) HEXAHYDRO-FURO[2,3-B]FURAN-3-OL

CROSS REFERENCE TO RELATED APPLICATIONS

This application is the national stage of Application No. PCT/EP2005/051452, filed Mar. 31, 2005, which claims priority from EPO Patent Application No. 04101336.8 filed 31 Mar. 2004, the entire disclosures of which are hereby incorporated in their entirely.

The present invention relates to methods for the preparation of (3R,3aS,6aR) hexahydro-furo[2,3-b]furan-3-ol as well as a novel intermediate, (3aR,4S,6aS) 4-methoxy-tetrahydro-furo[3,4-b]furan-2-one for use in said methods. More in particular the invention relates to a stereoselective method for the preparation of (3R,3aS,6aR) hexahydro-furo[2,3-b]furan-3-ol, and to a method amenable to industrial scaling up.

Hexahydro-furo[2,3-b]furan-3-ol is an important pharmacological moiety present in the structure of retroviral protease inhibitors such as those described by Ghosh et al. in *J. Med. Chem.* 1996, 39(17), 3278-3290, EP 0 715 618, WO 99/67417, and WO 99/65870. Said publications are hereby incorporated by reference.

Several methods for the preparation of hexahydro-furo[2,3-b]furan-3-ol are known.

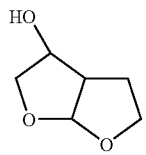

Ghosh et al. in *J. Med. Chem.* 1996, 39(17), 3278-3290, describe an enantioselective synthesis to obtain both (3R,3aS,6aR) and (3S,3aR,6aS) hexahydro-furo[2,3-b]furan-3-ol in optically pure form starting from 3(R)-diethyl malate and 3(S)-diethyl malate, respectively. Ghosh et al. also disclose the synthesis of a racemic mixture of the (3R,3aS,6aR) and (3S,3aR,6aS) enantiomers of hexahydro-furo[2,3-]furan-3-ol, starting from 2,3-dihydrofuran, followed by an enzymatic resolution of the final product. Pezeck et al. in *Tetrahedron Lett.* 1986, 27, 3715-3718, also describe a route for the synthesis of hexahydro-furo[2,3-b]-furan-3-ol using ozonolysis. Hexahydro-furo[2,3-b]furan-3-ol is also described as an intermediate in the synthesis of optically active perhydrofuro [2,3-b]furan derivatives in the publication by Uchiyama et al., in *Tetrahedron Lett.* 2001, 42, 4653-4656.

WO 03/022853 relates an alternative method which involves the synthesis of (3R,3aS,6aR) hexahydro-furo[2,3-b]furan-3-ol which method starts from a 2,3-diprotected-2,3-dihydroxy-propionaldehyde, which is transformed into a derivative encompassing a nitromethyl and one or two carboxylate moieties. Said derivative is subsequently transformed by a Nef reaction into a tetrahydrofuran compound, which is reduced and submitted to a intramolecular cyclization reaction to obtain the (3R,3aS,6aR) hexahydro-furo[2,3-b]furan-3-ol.

In order to transform the starting material, i.e. 2,3-diprotected-2,3-dihydroxy-propionaldehyde, into a derivative encompassing one or two carboxylate moieties, WO03/022853 describes different routes, which include a Wittig reaction using phosphorous ylides; a Horner-Emmons reaction using phosphonates in the presence of a base; a Knoevenagel type of condensation reaction using malonate derivatives; or alternatively applying Reformatsky reagents, i.e. precursors of —C(=O)—O— moieties such as cyanide. In particular, the examples disclosed therein, focus on two routes: the Knoevenagel and the Wittig routes.

The Knoevenagel route as illustrated in WO03/022853, consists of the addition of dimethyl malonate to a dry solution of the starting material 2,3-O-isopropylidene-glyceraldehyde to produce 2-(2,2-dimethyl-[1,3]dioxolan-4-ylmethylene)-malonic acid dimethyl ester with 2 carboxylates incorporated. Since the starting material is produced in aqueous solution, a laborious isolation procedure encompassing an extraction with tetrahydrofuran and water removal needs to be applied. This extraction and water removal require large amounts of tetrahydrofuran and production time. Further, the yield of the Knoevenagel reaction of 2,3-O-isopropylidene-glyceraldehyde to 2-(2,2-dimethyl-[1,3]dioxolan-4-ylmethylene)-malonic acid dimethyl ester exhibits a ceiling value of approximately 77% since intrinsically inevitable side reactions occur, even after optimization of conditions.

Due to the fact that the obtained di-carboxylated intermediate is a viscous oil, i.e. 2-(2,2-dimethyl-[1,3]dioxolan-4-ylmethylene)-malonic acid dimethyl ester, it needs to be introduced into the subsequent Michael addition as a solution in methanol. Methanol distillation after quench into aqueous NaHCO$_3$ solution, after the acidic Nef and cyclization reactions, but before extraction with an organic solvent such as ethyl acetate has disadvantages. Since the intermediate resulting from the acidic Nef and cyclization reactions, i.e. 4-methoxy-2-oxo-hexahydro-furo[3,4-b]furan-3-carboxylic acid methyl ester, is a labile compound in water, and the methanol distillation requires relatively high temperatures (up to 30° C. to 40° C.), decomposition of the intermediate occurs to polar compounds. These polar compounds remain in the aqueous phase and are further lost because they are not extracted to the organic phase. Since the methanol can not be removed prior to the extractions, a considerable volume is required in the work-up of 4-methoxy-2-oxo-hexahydro-furo[3,4-b]furan-3-carboxylic acid methyl ester.

During decarboxylation of 4-methoxy-2-oxo-hexahydrofuro[3,4-b]furan-3-carboxylic acid methyl ester there is significant by-product formation, i.e. (4-hydroxy-2-methoxy-tetrahydro-furan-3-yl)-acetic acid. Furthermore, crystallization of 4-methoxy-tetrahydro-furo[3,4-b]furan-2-one results in a brown solid due to concomitant polymerizations.

In addition, for the purification of 4-methoxy-tetrahydro-furo[3,4-b]furan-2-one, at least two acid-base extractive cascades are needed to remove the acid for the cyclization, thus resulting in an overall yield of 4-methoxy-tetrahydro-furo[3,4-b]furan-2-one of 52% based on 4-methoxy-2-oxo-hexahydro-furo[3,4-b]furan-3-carboxylic acid methyl ester, which is considered sub-optimal.

All the factors mentioned above disencourage the use of the Knoevenagel route. In fact, the decarboxylation step in this route presents an intrinsic disadvantage when compared to the Wittig route in that such decarboxylation step is not required with the latter.

WO03/022853 in Example I provides a Wittig route which employs triethyl phosphono acetate (TEPA) to obtain 3-(2,2-dimethyl-[1,3]dioxolan-4-yl)-acrylic acid ethyl ester. The subsequent Michael addition to 3-(2,2-dimethyl-[1,3]dioxolan-4-yl)-acrylic acid ethyl ester, presents limitations in that it produces a nitromethane adduct, i.e. 3-(2,2-dimethyl-[1,3]dioxolan-4-yl)-4-nitro-butyric acid ethyl ester, with a syn:anti ratio of approximately 8:2. Subsequent reduction followed by Nef/cyclization reactions yields the (3R,3aS,6aR) hexahydro-furo[2,3-b]furan-3-ol seriously contaminated with its exo-diastereoisomer, i.e. (3R,3aR,6aS) hexahydro-furo[2,3-b]furan-3-ol, with a ratio endo:exo of around 8:2. Although this process does not possess several of the disadvantages attached to the Knoevenagel process, it does not produce pure endo-diastereoisomer since there is no purification step available, such as crystallization, to remove the undesired exo-diastereoisomers that have been formed during the Michael addition in the anti configuration.

In the alternative Wittig route as disclosed in Example II of WO03/022853, the Michael addition product exhibits the same disadvantageous syn:anti ratio (8:2) as in Example I. The ethoxy intermediates (3aR,4S,6aS) 4-ethoxy-tetrahydro-furo[3,4-b]-furan-2-one and (3aR,4R,6aS) 4-ethoxy-tetrahydro-furo[3,4-b]furan-2-one obtained from the Nef/cyclization reaction were present in a (3aR,4S,6aS)/(3aR,4R,6aS) ratio of approximately 2.5/1, together with a significant amount of anti-isomers, i.e. with the syn:anti ratio of approximately 8:2. Purification of intermediates (3aR,4S,6aS) 4-ethoxy-tetrahydro-furo[3,4-b]furan-2-one and (3aR,4R,6aS) 4-ethoxy-tetrahydro-furo[3,4-b]furan-2-one by removal of the undesired anti-diastereoisomers by crystallization appears to be impossible to date. Reduction of the mixture and cyclization yielded (3R,3aS,6aR) hexahydro-furo[2,3-b]furan-3-ol, seriously contaminated with its exo-diastereoisomer, i.e. (3R,3aR,6aS) hexahydro-furo[2,3-b]-furan-3-ol, with an endo:exo ratio of approximately 8:2. Like the Wittig process of Example I above, this process does not posses several of the disadvantages attached to the Knoevenagel process, but in its present form does not yet provide pure (3R,3aS,6aR) hexahydro-furo[2,3-b]furan-3-ol in high industrial yields. Furthermore, the reactor volumes employed for the art-known procedures are large and the number of operations too high, said factors working in detriment of a cost-efficient process, and making thus processes not optimal for industrial scale.

There is thus a need for optimized processes for the industrial preparation of diastereomerically pure (3R,3aS,6aR) hexahydro-furo[2,3-b]furan-3-ol.

It has been surprisingly found that when a Wittig route is employed and the isomers of intermediate of formula (4) and (4') of WO03/022853 are produced in the methyl acetal form (i.e. R''' is methyl, and R'' is hydrogen), the yield of crude intermediate of formula (4) based on intermediate of formula (2) is much higher when compared to for instance the ethoxy- or isopropoxy-acetals (where R''' is ethyl or isopropyl, respectively and R'' is hydrogen).

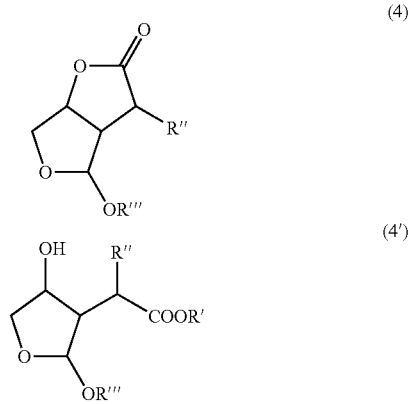

Moreover, it has been surprisingly found that this methyl acetal form of intermediate of formula (4) in the isomeric form (3aR,4S,6aS), can be crystallized from the mixture of the (3aR,4S,6aS) and (3aR,4R,6aS)-isomers of compound of formula (4) and the relatively large amount of isomers (4').

The increased yield and the possibility of crystallization of the isomeric form (3aR,4S,6aS) allows the production of (3R,3aS,6aR) hexahydro-furo[2,3-b]furan-3-ol in diastereomerically pure form and enhanced yield.

The compound of formula (4), (3aR,4S,6aS) 4-methoxy-tetrahydro-furo[3,4-b]furan-2-one, will be referred hereinunder as compound of formula α-(4) or alpha epimer or α-isomer. Likewise, (3aR,4R,6aS) 4-methoxy-tetrahydro-furo[3,4-b]furan-2-one will be referred hereinunder as compound of formula β-(4), or beta epimer or β-isomer.

compounds of formula (4)

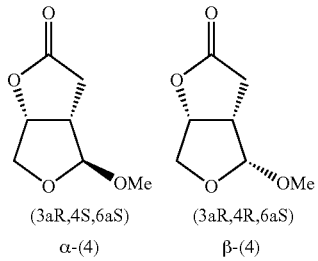

It is not only surprising that the methoxy acetal of formula α-(4) can be crystallized, but even more surprising that this crystallization is succesful in spite of the low alpha/beta ratio of less than 4/1 of the crude intermediates of formula (4) entering the crystallization. It should be realized that in the Knoevenagel process an alpha/beta ratio of at least 6:1 was required to have a crystallizable intermediate of formula α-(4).

Thus, the present invention provides an improved Wittig process and the use of the 4-alpha isomer of 4-methoxy-tetrahydro-furo[3,4-b]furan-2-one, in particular (3aR,4S,6aS), which significantly contributes into an amenable industrial preparation of (3R,3aS,6aR) hexahydro-furo[2,3-b]furan-3-ol in diastereomerically pure form.

Furthermore, it has been surprisingly found that a mixture in any ratio of the alpha and beta epimers of formula (4) can be transformed into a mixture of predominantly the alpha epimer, which can subsequently be isolated in pure form by crystallization. As such, the present invention provides a novel alkoxy-acetal epimerization of compound of formula (4) which significantly contributes into a cost-effective process for the preparation of (3R,3aS,6aR) hexahydro-furo[2,3-b]furan-3-ol.

In addition, it has also been surprisingly found that a mixture in almost any ratio of the alpha and beta epimers of formula (4) can be transformed in one single step into the crystalline alpha epimer by simultaneous crystallization and epimerization, also known as crystallization-induced asymmetric transformation. As such the present invention provides furthermore a simultaneous crystallization and epimerization for the isolation of pure (3aR,4S,6aS) 4-methoxy-tetrahydro-furo[3,4-b]furan-2-one.

SUMMARY

The present invention provides an improved Wittig process and the use of (3aR,4S,6aS) 4-methoxy-tetrahydro-furo[3,4- b]furan-2-one as an intermediate, more in particular in crystalline form, in the preparation of diastereomerically pure (3R,3aS,6aR) hexahydro-furo[2,3-b]furan-3-ol, which is suitable for industrial scaling up.

The present invention provides a novel alkoxy-acetal epimerization of compound of formula β-(4) to the compound of formula α-(4) which significantly contributes into a cost-effective process for the preparation of diastereomerically pure (3R,3aS,6aR) hexahydro-furo[2,3-b]furan-3-ol.

The present invention provides furthermore a simultaneous crystallization and epimerization for the isolation of diastereomerically pure (3aR,4S,6aS) 4-methoxy-tetrahydro-furo[3,4-b]furan-2-one.

Another embodiment of the invention provides with a method that allows the production of (3R,3aS,6aR) hexahydro-furo[2,3-b]furan-3-ol in a yield higher than for the methods described in the state of the art. Another object of the present invention is to provide with crystallizable and highly pure intermediate compounds, which are useful in the synthesis of diastereomerically pure (3R,3aS,6aR) hexahydro-furo[2,3-]furan-3-ol.

DETAILED DESCRIPTION OF THE INVENTION

The present invention relates to a method for the synthesis of (3R,3aS,6aR) hexahydro-furo[2,3-b]furan-3-ol having the structure of formula (6),

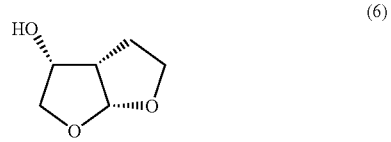
(6)

which method comprises the use of intermediates of formula (4).

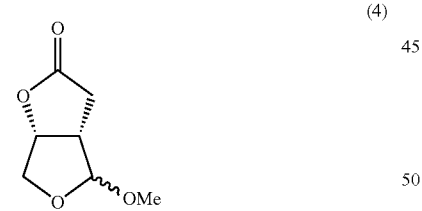
(4)

The present invention also relates to a method for the synthesis of (3R,3aS,6aR) hexahydro-furo[2,3-b]furan-3-ol having the structure of formula (6),

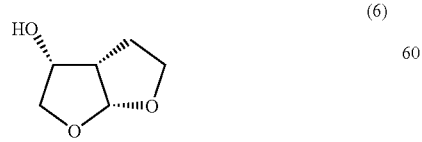
(6)

which method comprises the use of intermediate of formula α-(4).

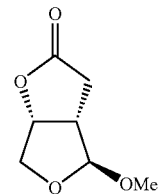
α-(4)

The present invention further relates to a method for the synthesis of (3R,3aS,6aR) hexahydro-furo[2,3-b]furan-3-ol having the structure of formula (6), (6)

which method comprises the steps of:
a) treating compound of formula (3) with a base and subsequently with an acid in the presence of methanol, (3)

wherein
P$^1$ and P$^2$ are each independently a hydrogen, a hydroxy-protecting group or may together form a vicinal-diol protecting group,
R$^1$ is alkyl, aryl or aralkyl;
resulting in intermediates of formula (4); and (4)

b) reducing intermediates of formula (4) with a reducing agent and applying an intramolecular cyclization reaction to obtain compound of formula (6).

In one embodiment, the present invention relates to a method for the synthesis of (3R,3aS,6aR) hexahydro-furo[2,3-b]furan-3-ol having the structure of formula (6), (6)

which comprises the steps of:

a) treating compound of formula (3) with a base and subsequently with an acid in the presence of methanol,

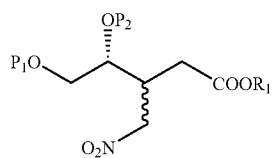
(3)

wherein
P¹ and P² are as defined above,
R¹ is as defined above;
resulting in intermediates of formula (4);

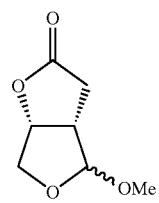
(4)

b) crystallizing with a solvent intermediate of formula α-(4); and

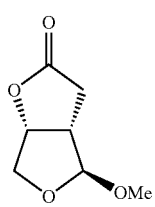
α-(4)

c) reducing intermediate of formula α-(4) with a reducing agent and applying an intramolecular cyclization reaction to obtain compound of formula (6).

In another embodiment, the present invention relates to the epimerization with acid of compound of formula β-(4) into compound of formula α-(4).

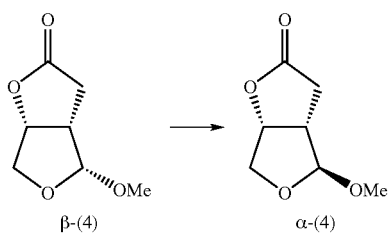

In another embodiment, the present invention relates to a method for the synthesis of (3R,3aS,6aR) hexahydro-furo[2,3-b]furan-3-ol having the structure of formula (6),

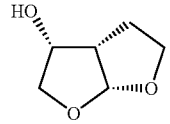
(6)

which comprises the steps of:

a) treating intermediate of formula (3) with a base and subsequently with an acid in the presence of methanol;

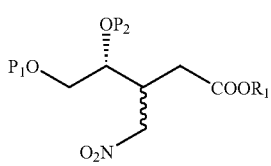
(3)

wherein
P¹ and P² are as defined above,
R¹ is as defined above;
resulting in intermediates of formula (4);

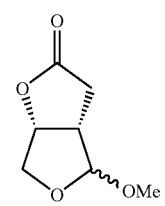
(4)

b) epimerizing with acid the intermediate of formula β-(4) into the intermediate of formula α-(4);

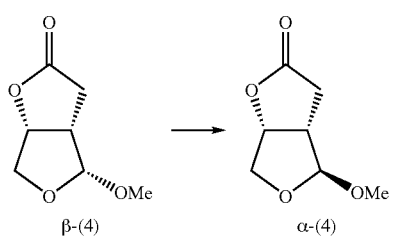
β-(4)    α-(4)

c) crystallizing with a solvent intermediate of formula α-(4); and

α-(4)

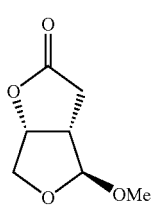

d) reducing intermediate of formula α-(4) with a suitable reducing agent and applying an intramolecular cyclization reaction to obtain compound of formula (6).

In another embodiment, the present invention relates to a method for the synthesis of (3R,3aS,6aR) hexahydro-furo[2,3-b]furan-3-ol having the structure of formula (6),

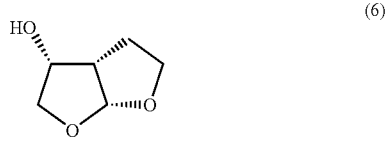
(6)

which comprises the steps of:
a) treating said intermediate of formula (3) with a base and subsequently with an acid in the presence of methanol;

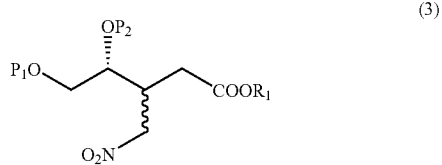
(3)

wherein
$P^1$ and $P^2$ are as defined above,
$R^1$ is as defined above;
resulting in intermediates of formula (4);

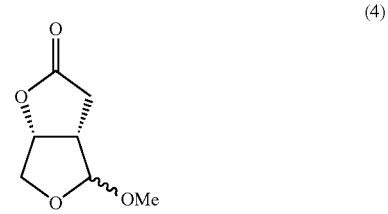
(4)

b) crystallizing with a solvent intermediate of formula α-(4);

α-(4)

c) epimerizing with acid the intermediate of formula β-(4) in the mother liquor of above-mentioned crystallization into the intermediate of formula α-(4);

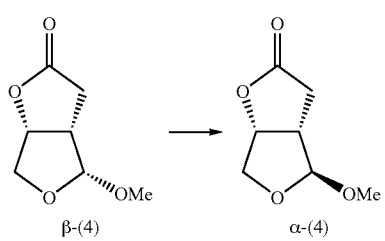

d) crystallizing with a solvent intermediate of formula α-(4), giving a second crop of intermediate of formula α-(4); and

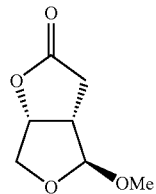
α-(4)

e) reducing intermediate of formula α-(4) with a suitable reducing agent and applying an intramolecular cyclization reaction to obtain compound of formula (6).

In yet another embodiment, the present invention relates to a method for the synthesis of (3R,3aS,6aR) hexahydro-furo[2,3-b]furan-3-ol of formula (6), as described in the methods above wherein the epimerization and crystallization of compound of formula α-(4) occur simultaneously.

The present invention further provides a method for the synthesis of (3R,3aS,6aR) hexahydro-furo[2,3-b]furan-3-ol of formula (6), as described in the methods above wherein compound of formula (3) is obtained by reacting compound of formula (2) with nitromethane and a base.

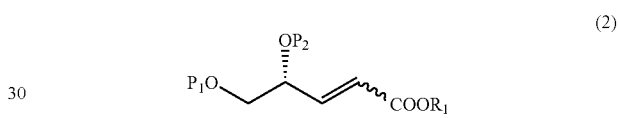
(2)

And yet in another embodiment, the present invention provides a method for the synthesis of (3R,3aS,6aR) hexahydro-furo[2,3-b]furan-3-ol of formula (6), as described in the methods above wherein compound of formula (2) is obtained by condensing an intermediate of formula (1), or its hydrate, hemihydrate or a mixture thereof, with phosphonates of the formula $(R^6O)_2P(=O)-CH_2-C(=O)OR^1$, wherein
$P^1$ and $P^2$ are as defined above,
$R^1$ is as defined above,
$R^6$ is alkyl, aryl or aralkyl,

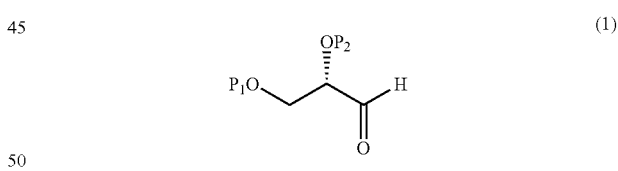
(1)

The term "hydroxy-protecting group" as used herein refers to a substituent which protects hydroxyl groups against undesirable reactions during synthetic procedures such as those O-protecting groups disclosed in Greene and Muts, "Protective Groups In Organic Synthesis," (John Wiley & Sons, New York, 3$^{rd}$ edition, 1999). Hydroxy-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyl-dimethylsilyl and t-butyldiphenylsilyl; and esters, for example, acetate, propionate, benzoate and the like.

The term "vicinal-diol protecting group" as used herein refers to protecting groups in the acetal or ketal form and in the orthoester form. Specific examples of the protecting group in the acetal or ketal radical form include methylene, diphenylmethylene, ethylidene, 1-t-butylethylidene, 1-phenylethylidene, (4-methoxyphenyl)ethylidene, 2,2,2-trichloroethylidene, isopropylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene, etc. and specific examples of the protecting group in the orthoester form include methoxymethylene, ethoxymethylene, 1-methoxyethylidene, 1-ethoxyethylidene, 1,2-dimethoxy-ethylidene, alpha-methoxybenzylidene, 1-(N,N-dimethylamino)ethylidene, alpha-(N,N-dimethylamino)benzylidene, 2-oxacyclopentylidene, etc. In a preferred embodiment, the vicinal-diol protecting group is isopropylidene.

The term "alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_{1-20}$alkyl), suitably 1 to 10 carbon atoms ($C_{1-10}$alkyl), preferably 1 to 8 carbon atoms ($C_{1-8}$alkyl), more preferably 1 to 6 carbon atoms ($C_{1-6}$alkyl), and even more preferably 1 to 4 carbon atoms ($C_{1-4}$alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

The term "alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl and the like.

The term "alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butynyl and the like.

The term "aryl" as used herein, alone or as part of a group, includes an organic radical derived from an aromatic hydrocarbon by removal of one hydrogen, and includes monocyclic and polycyclic radicals, such as phenyl, biphenyl, naphthyl.

The term "alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy and the like.

The terms "aralkyl" and "aralkoxy" as used herein, alone or in combination, mean an alkyl or alkoxy radical as defined above in which at least one hydrogen atom is replaced by an aryl radical as defined above, such as benzyl, benzyloxy, 2-phenylethyl, dibenzylmethyl, hydroxyphenylmethyl, methylphenylmethyl, and the like.

The term "aralkoxycarbonyl" as used herein, alone or in combination, means a radical of the formula aralkyl-O—C(O)— in which the term "aralkyl" has the meaning given above. Examples of an aralkoxycarbonyl radical are benzyloxycarbonyl and 4-methoxy-phenylmethoxycarbonyl.

The term "cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl and the like.

The term "cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1cyclopentylethyl, 1-cyclohexylethyl, 2-cyclopentylethyl, 2-cyclohexylethyl, cyclobutylpropyl, cyclopentylpropyl, cyclohexylbutyl and the like.

The terms "heterocycloalkyl" as used herein, alone or in combination, refers to a saturated or partially unsaturated monocyclic, bicyclic or tricyclic heterocycle having preferably 3 to 12 ring members, more preferably 5 to 10 ring members and most preferably 5 to 6 ring members, which contains one or more heteroatom ring members selected from nitrogen, oxygen and sulphur, and which is optionally substituted on one or more carbon atoms by halogen, alkyl, alkoxy, hydroxy, oxo, aryl, aralkyl and the like, and/or on a secondary nitrogen atom (i.e., —NH—) by hydroxy, alkyl, aralkoxycarbonyl, alkanoyl, phenyl or phenylalkyl and/or on a tertiary nitrogen atom (i.e., =N—) by oxido. Heterocycloalkyl also includes benzfused monocyclic cycloalkyl groups having at least one such heteroatom. Heterocycloalkyl in addition to sulfur and nitrogen also includes sulfones, sulfoxides and N-oxides of tertiary nitrogen containing heterocycloalkyl groups.

The term "heteroaryl" as used herein, alone or in combination, refers to an aromatic monocyclic, bicyclic, or tricyclic heterocycloalkyl radical as defined above and is optionally substituted as defined above with respect to the definitions of aryl and heterocycloalkyl.

Examples of such heterocycloalkyl and heteroaryl groups are pyrrolidinyl, piperidinyl, piperazinyl, morpholinyl, thiamorpholinyl, pyrrolyl, imidazol-4-yl, 1-benzyloxy-carbonylimidazol-4-yl, pyrazolyl, pyridyl, 2-(1-piperidinyl)-pyridyl, 2-(4-benzyl-piperazin-1-yl-1-pyridinyl), pyrazinyl, pyrimidinyl, furyl, tetrahydrofuryl, thienyl, triazolyl, oxazolyl, thiazolyl, 2-indolyl, 2-quinolinyl, 3-quinolinyl, 1-oxido-2-quinolinyl, isoquinolinyl, 1-isoquinolinyl, 3-isoquinolinyl, tetrahydroquinolinyl, 1,2,3,4-tetrahydro-2-quinolyl, 1,2,3,4-tetrahydroisoquinolinyl, 1,2,3,4-tetrahydro-1-oxo-isoquinolinyl, quinoxalinyl, 2-benzofurancarbonyl, 1-, 2-, 4- or 5-benzimidazolyl, and the like.

The term "silyl" as used herein refers to a silicon atom optionally substituted by one or more alkyl, aryl and aralkyl groups.

The terms "isomer", "isomeric form", "stereochemically isomeric forms" or "stereoisomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

The term "diastereomer" or "diastereomeric form" applies to molecules with identical chemical constitution and containing more than one stereocenter, which differ in configuration at one or more of these stereocenters.

The term "epimer" in the present invention refers to molecules with identical chemical constitution and containing more than one stereocenter, but which differ in configuration at only one of these stereocenters. In particular, the term "epimer" is intended to include compounds of formula (4) which differ in the orientation of the bond between carbon 4 (C-4), and the methoxy substituent, i.e. compounds of formula α-(4) and β-(4), respectively, where the C-4 is 4S and 4R, respectively.

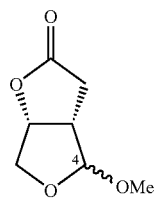

(4)

Pure stereoisomeric forms of the intermediate of formula (1), (4), (6) and of the starting material as mentioned herein are defined as isomers substantially free of other enantiomeric or diastereomeric forms of the same basic molecular structure of said compounds or starting material. Suitably, the term "stereoisomerically pure" compounds or starting material relates to compounds or starting material having a stereoisomeric excess of at least 50% (i.e. minimum 75% of one isomer and maximum 25% of the other possible isomers) up to a stereoisomeric excess of 100% (i.e. 100% of one isomer and none of the other), preferably, compounds or starting material having a stereoisomeric excess of 75% up to 100%, more preferably, compounds, starting material or reagents having a stereoisomeric excess of 90% up to 100%, even more preferred compounds or intermediates having a stereoisomeric excess of 94% up to 100% and most preferred, having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

As such, a preferred embodiment employs S-2,3-O-isopropylidene-glyceraldehyde as starting material in an enantiomeric excess of more than 95%, more preferably in an enantiomeric excess of more than 97%, even more preferably in an enantiomeric excess of more than 99%.

Compounds of Formula (1)

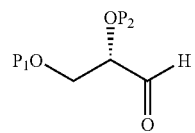

(1)

Compounds of formula (1) may be obtained from commercially available sources. The synthesis of compounds of formula (1) either in enantiomerically pure form or in racemic form has been described in the literature. For example, the preparation of 2,3-O-isopropylidene-S-glyceraldehyde is described in C. Hubschwerlen, *Synthesis* 1986, 962; the preparation of 2,3-O-isopropylidene-R-glyceraldehyde is described in C. R. Schmid et al., *J. Org. Chem.* 1991, 56, 4056-4058; and the preparation of 2,3-O-isopropylidene-(R, S)-glyceraldehyde is described in A. Krief et al., *Tetrahedron Lett.* 1998, 39, 1437-1440. Thus, said intermediate of formula (1) may be purchased, prepared prior to the reaction or formed in situ. In a preferred embodiment, said compound is formed in situ by, for instance, oxidation in aqueous or partially aqueous solution. In case said compound is in aqueous or partially aqueous solution it is usually partially present in the hydrate or hemihydrate forms thereof.

Suitably, the invention relates to a method wherein $P^1$ and $P^2$ together form a vicinal-diol protecting group, and particularly, which is an acid labile protecting group that remains unaffected during the base treatment step of the subsequent Nef reaction. Preferably, said vicinal-diol protecting group is selected from the group consisting of methylene, diphenylmethylene, ethylidene, 1-t-butylethylidene, 1-phenylethylidene, (4-methoxyphenyl)ethylidene, 2,2,2-trichloroethylidene, isopropylidene, cyclo-pentylidene, cyclohexylidene, cycloheptylidene, benzylidene, p-methoxybenzylidene, 2,4-dimethoxybenzylidene, 3,4-dimethoxybenzylidene and 2-nitrobenzylidene. In a more preferred embodiment, $P^1$ and $P^2$ together form a dialkyl methylene such as an isopropylidene or a 3-pentylidene radical. In the most preferred embodiment $P^1$ and $P^2$ together form an isopropylidene radical. A specific advantage of the use of isopropylidene compared to other protecting groups is that the reagents required for the diol protection, i.e. dimethoxypropane, 2-methoxypropene or acetone, are commercially available and inexpensive.

Interesting vicinal-diol protecting groups are those protecting groups that do not cause one or more additional stereogenic centers in the intermediates of formula (1), (2), and (3).

The above-mentioned hydroxy-protecting group and vicinal-diol protecting groups can be readily cleaved by methods known in the art such as hydrolysis, reduction, etc., which are appropriately selected depending on the protecting group used. According to a more preferred embodiment, the vicinal-diol protecting group is an acid labile protecting group, wherein the term "acid labile" as used herein refers to vicinal-diol protecting groups that are readily cleaved using acidic conditions.

Compounds of Formula (2)

(2)

Compounds of formula (1) or their hydrate, hemihydrate or mixtures thereof are subsequently transformed to compounds of formula (2) by means of phosphonates in the presence of a base. The reaction employs phosphonates of the formula $(R^6O)_2P(=O)-CH_2-C(=O)OR^1$, wherein $R^1$ is alkyl, aryl or aralkyl, $R^6$ is alkyl, aryl or aralkyl.

Suitably, $R^1$ is $C_{1-6}$alkyl, aryl or aryl$C_{1-6}$alkyl, in particular, $C_{1-6}$alkyl, more in particular, $R^1$ is methyl, ethyl, propyl, isopropyl, n-butyl, isobutyl, sec-butyl, tert-butyl and pentyl, preferably, $R^1$ is methyl, ethyl or tert-butyl, and most preferably $R^1$ is ethyl.

Examples of phosphonates include ethyl 2-(diethylphosphono)propionate, ethyl 2-(dimethylphosphono)propionate, triethyl phosphonoacetate (TEPA), amongst others.

Preferably, compound of formula (1) and the phosphonate are present in the reaction mixture in a range of about 0.9:1.1 to about 1.1:0.9 molar ratio, most preferably in a molar ratio of about 1:1. When compound of formula (1) is prepared in situ, its contents in the reaction mixture should be determined and based thereupon about 1 equivalent of phosphonate is added.

Suitable temperatures for the condensation reaction range between about −5° C. and about 50° C., preferably between about −2° C. and about 35° C., more preferably between about 0° and about 25° C.

Examples of suitable bases that may be employed for the conversion of compound of formula (1) into compounds of formula (2) include, but are not limited to, alkylamines, sodium, potassium, lithium or cesium carbonates or sodium, potassium, lithium or cesium hydroxide or alkoxides, and mixtures thereof. Preferably the base is potassium carbonate, even more preferably, the base is added as a solid and not as a solution in water. Also more preferably, the amount of potassium carbonate as a solid is at least about 2.5 equivalents based on compound of formula (1).

Preferably the pH of the reaction mixture is kept within a range of about 7 to about 13, more preferably within a range of about 8 to about 12, even more preferably the pH is kept between about 9 and about 11.

Suitable solvents for this reaction are water, any hydrocarbon, ether, halogenated hydrocarbon, or aromatic solvents known in the art for condensation reactions. These would include, but are not limited to, pentane, hexane, heptane, toluene, xylene(s), benzene, mesitylene(s), t-butylmethyl ether, dialkyl ethers (ethyl, butyl), diphenyl ether, chlorobenzene, methylene chloride, chloroform, carbon tetrachloride, acetonitrile, dichlorobenzene, dichloroethane, trichloroethane, cyclohexane, ethylacetate, isopropyl acetate, tetrahydrofuran, dioxane, methanol, ethanol, and isopropanol. Preferably water is used as the solvent, either as the only solvent or as a mixture with another solvent, for instance with tetrahydrofuran.

In one embodiment, a work-up procedure may be applied on the reaction mixture containing compounds of formula (2) by separating the organic and aqueous phases and subsequently extracting from the aqueous phase an additional portion of compounds of formula (2) with an organic solvent, different from the organic phase. As such, the tetrahydrofuran phase may be separated from the aqueous phase and the latter may be extracted with for instance two portions of toluene. Preferred solvents for the extraction are ethyl acetate, toluene, tetrahydrofuran. Most preferred solvent is toluene.

Compounds of formula (2) are preferably not purified on silica gel. Although this produces less pure compounds of formula (2) than the silica-gel purified product, the quality is sufficient to produce compound of formula (4) with satisfactory quality and yield. The non-purification eventually aids in simplifying the industrial process of the present invention.

Compounds of formula (2) can be obtained in 2 isomeric forms, the E and the Z isomers with E being the preferred isomer.

Compounds of Formula (3)

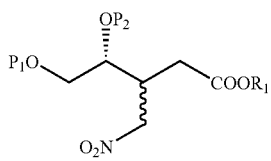

(3)

Compounds of formula (2) can be subsequently submitted to a Michael addition, in which nitromethane is added as a formyl group precursor to the α,β-unsaturated ester intermediates of formula (2), together with a base.

Nitromethane is commercially available as a solution in methanol, and is preferred in such composition.

Examples of bases that are suitable for catalyzing Michael additions are sodium, potassium, lithium, cesium hydroxide or alkoxides, TBAF (tetra-n-butylammonium fluoride), DBU (1,8-diazabicyclo[5.4.0]undec-7-ene), TMG (1,1,3,3-tetramethyl-guanidine), preferably sodium hydroxide, potassium hydroxide, lithium hydroxide, sodium methoxide, lithium methoxide, TBAF, DBU, TMG and mixtures thereof, more preferably DBU and TMG and most preferably DBU.

When DBU is employed as the base in the conversion of compounds of formula (2) to compounds of formula (3), suitably the amount of base added is higher than about 0.5 equivalents based on compounds of formula (2), more preferably higher than about 0.8 equivalents, even more preferably between about 0.8 and about 1.2 equivalents, most preferably between about 0.9 and about 1.1 equivalents. In a preferred embodiment, DBU is present in approximately 1 equivalent.

Any solvent suitable for carrying out a Michael addition may be employed. Examples of suitable solvents are methanol, ethanol and acetonitrile. Preferably, the solvent is methanol, which allows the performance of a one-pot procedure with the subsequent transformations of the obtained compounds of formula (3) into compounds of formula (4).

The syn addition form of the compound of formula (3) is predominantly present. The syn/anti ratio is approximately 8/2.

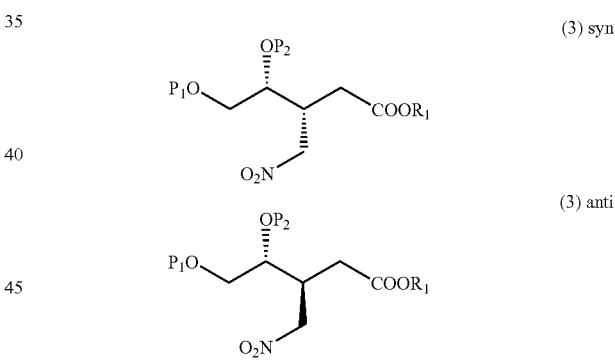

Compounds of Formula (4)

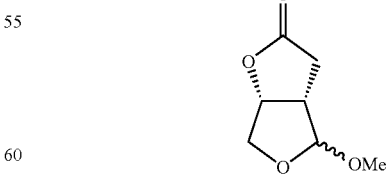

(4)

Compounds of formula (4), i.e. α-(4) and β-(4), are obtained by a number of transformations starting from compounds of formula (3) and consisting of a Nef reaction into the corresponding formyl derivative, simultaneous acid-catalyzed deprotection of the diol and two cyclization reactions.

These transformations are accomplished by treating intermediates of formula (3) with a base and subsequently treating the reaction mixture with an acid in the presence of methanol, preferably by adding or pouring the reaction mixture to an acid in the presence of methanol, resulting in intermediates of formula (4). The reactions mentioned above also produce compounds of formula (4').

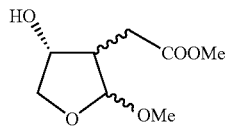

(4')

In the Nef reaction, a primary or a secondary nitroalkane is converted into the corresponding carbonyl compound (N. Kornblum Organic reactions 1962, 12, 101 and H. W. Pinnick Organic Reactions 1990, 38, 655). In the classical procedure, the nitroalkane is deprotonated with a base at the α-position to the nitro function, followed by acid-catalyzed hydrolysis of the intermediate 'nitronate' salt via addition to a strong acid present in excess, to give the carbonyl derivative.

Suitable bases may be selected by one of skill in the art of organic synthesis. Suitable bases include, but are not limited to, inorganic bases such as alkali metal, alkali earth metal, and ammonium hydroxides and alkoxides. Examples of suitable bases are lithium diisopropyl amide, sodium methoxide, potassium methoxide, lithium methoxide, potassium t-butoxide, calcium dihydroxide, barium dihydroxide, and quaternary alkylammonium hydroxides, DBN (1,3-diazabicyclo[3.4.0]non-5-ene), DBU, DABCO (1,4-diazabicyclo[2.2.2]octane), TBAF, TMG, potassium carbonate and sodium carbonate or mixtures thereof. Preferred bases are sodium methoxide, potassium methoxide, lithium methoxide, TBAF, DBU, TMG, or mixtures thereof, more preferred bases are sodium methoxide, lithium methoxide, DBU or TMG or mixtures thereof, and most preferred is sodium methoxide.

As an acid, any acid may be employed, preferably a strong acid, more preferably a mineral acid such as concentrated sulfuric acid, concentrated hydrochloric acid, and most preferably concentrated sulfuric acid.

By using anhydrous conditions or almost anhydrous conditions and methanol as the solvent in the Nef reaction, the cyclic methyl acetal of the formyl group is obtained. The methyl substituents in the intermediates of formula (4) and (4') originate from the methanol solvent.

Alternatively, if the Nef and the previous Michael addition are carried out in a non-methanolic solvent, for example acetonitrile, other acetals than compounds of formula (4) and (4') will be obtained instead, usually a mixture of the hemiacetals and the alkyl acetals corresponding to the $R^1$ substituent in compounds of formula (3). Said hemiacetal and acetal congeners may be transformed into the desired methyl acetals of formula (4) and (4') by newly reacting those with methanol under acidic conditions.

Alternatively, when the previous Michael addition is performed with DBU or TMG and compounds of formula (3) are not isolated and the subsequent Nef reaction is carried out with a strong base, in particular with sodium methoxide or lithium methoxide, surprisingly a significant increase in the yield of compounds of formula (4) is obtained. As such, the presence of DBU or TMG during the Nef reaction with a strong base is a preferred embodiment of this invention.

For instance, when the Michael addition with nitromethane is carried out in methanol with hydroxides, alkoxides or TBAF in various amounts, the yield of compounds of formula (3) based on compounds of formula (2) is approximately 80%. When the subsequent Nef and cyclizations are carried out with non-isolated compounds of formula (3) using sodium methoxide as the additional base and sulphuric acid in methanol as the acidic solution, 43% of compound of formula (4) can be obtained based on compounds of formula (2) with an α(4)/β(4) ratio of at least approximately 3/1.

When the Michael addition is carried out with approximately 1 equivalent of DBU or TMG based on compounds of formula (2), the yield of compounds of formula (3) based on compounds of formula (2) is also approximately 80%. However, when the Nef and cyclization reactions are subsequently carried out with non-isolated compounds of formula (3), combined with 1.0 equivalents of sodium or lithium methoxide based on compounds of formula (2), compound of formula (4) may be obtained in 53-58% yield based on compounds of formula (2) with an α(4)/β(4) ratio of at least approximately 3/1.

The bicyclic intermediates of formula (4) are the expected cyclization products originating from intermediates of formula (3) in a syn configuration. The intermediates of formula (4') are the expected reaction products originating from intermediate of formula (3) in the anti configuration, which does not cyclize, and also the expected reaction products originating from intermediate of formula (3) in a syn configuration, since the cyclization of the syn isomers is usually not fully complete. The trans-configuration of the substituents at carbon atom number 3 (C-3) and carbon atom number 4 (C-4) on the tetrahydrofuran ring of intermediate of formula (4') prevents the lactone ring formation as observed in intermediates of formula (4).

Preferably the acidic quench of the Nef and cyclization reactions is performed with an excess of concentrated sulfuric acid, preferably with 2 to 10 equivalents based on compounds of formula (2), more preferably with 2.5 to 5 equivalents, even more preferably with 3 to 4 equivalents and most preferably with approximately 3.5 equivalents, as a 20 wt % to 80 wt % solution in methanol, preferably as a 40 wt % to 60 wt % solution in methanol. A larger excess of sulphuric acid causes a higher alpha/beta ratio for compounds of formula (4) but also requires more base for the subsequent neutralization in the alkaline quench. For instance, when 3.5 equivalents of sulphuric acid based on compounds of formula (2) are used in the acidic quench as a 50 wt % solution in methanol, an α(4)/β(4) ratio of up to 4/1 may be achieved.

The acidic quench of the Nef and cyclization reactions can be carried out at temperatures that range between about −40° C. and about 70° C., preferably at temperatures between about −25° C. and about 15° C., more preferably at temperatures between about −20° C. and about 5° C., most preferably at temperatures between about −15° C. and about 0° C. The reaction times can range up to about 24 hours, suitably in a range between about 15 minutes and about 12 hours, even more suitably in a range between about 20 minutes and about 6 hours.

For the isolation of compounds of formula (4), an aqueous work-up may be required to remove the salts and part of the intermediates of formula (4'). A base will neutralize the acid previously employed, since acidic aqueous conditions would cause hydrolysis of the methyl acetal of compound of formula (4) to the hemiacetal congener, thus resulting in product loss. As such, isolation of compound of formula (4) is optimally carried out by an alkaline quench reaction, preferably by an aqueous alkaline quench reaction, followed by extraction of compound of formula (4) with a water-immiscible organic solvent. Preferably, the acidic mixture resulting from the Nef and cyclization reactions is added to the alkaline aqueous solution.

Since during the alkaline aqueous quench reaction, a large reactor volume is needed, it is preferable to minimize said volume as much as possible. This may be accomplished in different ways, like for instance employing highly soluble bases, or using bases in slurry form. As such, suitable bases for the work-up of compound of formula (4) are a bicarbonate or carbonate, preferably sodium, potassium, lithium or cesium bicarbonate, preferably sodium, potassium, lithium or cesium bicarbonate, even more preferably sodium or potassium bicarbonate, most preferably potassium bicarbonate, either completely in solution or as a slurry. As such, the use of saturated potassium hydrogen carbonate solution for the alkaline quench instead of saturated sodium hydrogen carbonate solution has, due to its higher solubility, the advantage that the volume of the aqueous phase can be further reduced and the formed potassium sulphate has surprisingly a much better filterability than the sodium sulphate.

Advantageously, during the alkaline quench the pH is kept between about 2 and about 9, preferably between about 3 and about 8, more preferably between about 3.5 and about 7.5. Also advantageously, at the end of the alkaline quench the pH is set between about 3.5 and about 6, preferably between about 3.5 and about 5, most preferably between about 3.8 and about 4.5. These required pH ranges may be accomplished by the use of carbonates and bicarbonates as indicated above. Optionally, additional base or acid may be used to set the pH at a certain value at the end of the quench reaction. Within the preferred pH range, the methanol can be evaporated from the reaction mixture after the alkaline quench and before the extractions with organic solvent at temperatures between about 0° and about 65°, preferably between about 20° and about 45° C. Under these conditions compounds of formula (4) are not degraded, even when large scale residence times are applied. Methanol removal by evaporation before the extractions with organic solvent has the advantage that the extraction efficiency significantly increases, so that less organic solvent is consumed and the productivity further increases.

Suitable organic non-water miscible solvents are any ester, hydrocarbon, ether, halogenated hydrocarbon, or aromatic solvents. These would include, but are not limited to, pentane, hexane, heptane, toluene, xylene(s), benzene, mesitylene(s), t-butylmethyl ether, dialkyl ethers (ethyl, butyl), diphenyl ether, chlorobenzene, dichloromethane, chloroform, carbon tetrachloride, acetonitrile, dichlorobenzene, 1,2-dichloroethane, 1,1,1-trichloroethane, ethyl acetate, isopropyl acetate, preferably ethylacetate.

In order to improve the extraction yield of compounds of formula (4), water soluble salts may be added to the mixture prior to extraction. A preferable salt includes NaCl.

One advantage of the method disclosed in the present invention when compared to the Knoevenagel route of the prior art is that during the alkaline aqueous quench it is not necessary to simultaneously extract compounds of formula (4) with an organic solvent. The absence of the organic solvent during the alkaline quench further aids in diminishing the reactor volume and the filtration of the inorganic salts formed is much easier. In the Knoevenagel route, the presence of organic solvent during the alkaline quench is required if product loss is to be avoided.

To further isolate compound of formula α-(4) in pure form, crystallization of said compound may be applied.

Crystallization

Compound of formula α-(4) may be crystallized from a solvent, such as organic, inorganic solvents or water, and mixtures thereof. Suitable solvents for crystallization include isopropanol, t-amyl alcohol, t-butanol, ethylacetate, ethanol and methyliso-butylketone. Especially isopropanol, t-amyl alcohol, and t-butanol are preferred as they produce a high crystallization yield and product with high purity. More preferably isopropanol or t-amyl alcohol are used, most preferably isopropylalcohol.

If isopropylalcohol is the solvent used in the crystallization, the preferred concentration before the crystallization of compound of formula α-(4) is between about 5 to about 30 wt %, more preferably between about 10 and about 25 wt %, even more preferably between about 15 and about 20 wt %.

Crystallization affords compound of formula α-(4) in high purity although small amounts of compound of formula β-(4) may be present, i.e. in less than about 5%, in particular in amounts less than about 3%.

Epimerization

Compound of formula (4) in its beta isomeric form may be epimerized into compound of formula α-(4) with an acid, for instance with organic or inorganic acids, preferably in the absence of water and in the presence of methanol.

Epimerization is preferably performed with $MeSO_3H$ in methanol, or any comparable acid with a similar acidic strength since this prevents the formation of side products. Preferably, the amount of $MeSO_3H$ in methanol employed ranges between about 0.05 and about 1.5 equivalents, based on compounds of formula (4), more preferably between about 0.1 and about 0.3 equivalents.

The temperature for carrying out the epimerization is between about 0° C. and around reflux temperature, preferably between about 20° C. and around reflux temperature, more preferably between about 40° C. and around reflux temperature, even more preferably at around reflux temperature.

Several alternatives may exist for some of the processes described above. For instance, in one embodiment, after obtaining a mixture of compound of formula α-(4) and a compound of formula β-(4), the compound of formula α-(4) is crystallized and the synthetic procedure is continued to produce compound of formula (6). In another embodiment, the artisan may choose to crystallize compound of formula α-(4), proceed with an epimerization of the remaining mother liquour, which contains a relatively large amount of the undesired β-(4) epimer, to obtain a mixture with a relatively large amount of the α-(4) epimer, and apply a second crystallization of the α-(4) epimer. For instance, when the crude mixture of compound of formula (4) having a α-(4)/β-(4) ratio ranging between about 3.5/1 to about 4/1, is crystallized, a first crop of α-(4) is isolated and the remaining mother liquor has a α-(4)/β-(4) ratio ranging between about 0.3/1 and about 1.5/1. After epimerization of the β-(4) epimer, the α-(4)/β-(4) ratio in the mother liquor is approximately 3/1 and a second crop of α-(4) is obtained by crystallization having at least a comparable purity as the first crop of α-(4).

Alternatively, one may proceed by performing a simultaneous crystallization of the α-(4) epimer and epimerization reaction of the β-(4) to the α-(4) epimer. In another embodiment, one may start by epimerizing the β-(4) to the α-(4) epimer, and subsequently crystallizing the α-(4) epimer. In yet another embodiment, one may start by epimerizing the β-(4) to the α-(4) epimer, subsequently crystallizing the α-(4) epimer, applying a second epimerization of the remaining mother liquour and an additional crystallization giving a second crop of the α-(4) epimer.

As such, in one embodiment, the mother liquor of a previous crystallization of compound of formula α-(4) from isopropanol may be epimerized by evaporation of the isopropanol, taking up the residue in methanol and reflux for approximately 30 minutes to about 4 hours with MeSO₃H, preferably with about 0.1 to about 0.3 equivalents. If the reaction mixture is subsequently poured into aqueous NaHCO₃, extracted with EtOAc and the organic phase solvent-switched to isopropanol, a second portion of pure compound of formula α-(4) may be obtained by crystallization.

In a preferred embodiment, a mixture of the α-(4) and β-(4) epimers may be transformed in one step into 100% or almost 100% alpha isomer in 100% or almost 100% yield, so without by-product formation, via a direct crystallization of the α-(4) epimer and simultaneous epimerization of the β-(4) to the α-(4) epimer, also known as crystallization-induced asymmetric transformation. A crystallization-induced asymmetric transformation may be accomplished by solving the mixture of the α-(4) and β-(4) epimers in methanol in the presence of approximately 0.010 equivalents MeSO₃H, based on the sum of both epimers, and evaporating the methanol in vacuo at about 30° C. to about 40° C. This embodiment is particularly preferable since the mixture of the α-(4) and B-(4) epimers can be transformed to only the α-(4) epimer in one step which has lower production costs and one batch of α-(4) with homogeneous quality is obtained.

In a preferred embodiment neutralization of the acid, such as MeSO₃H, is performed prior to the solvent switch from methanol to the crystallization solvent such as isopropanol. Said neutralization may be accomplished by adding a slight molar excess of a base, based on the epimerization acid used. As a base, any base can be used as long as the salt of the base with the epimerization acid does not contaminate the crystals of the α-(4) epimer. For instance, in case MeSO₃H is used as the epimerization acid, a tertiary amine may be used, preferably triethylamine, giving the triethylammonium methanesulfonate salt, which does not contaminate the crystals of the α-(4) epimer during the crystallization from isopropanol. The addition of a slight excess of NEt₃ over MeSO₃H for the neutralization, avoids the formation of isopropyl acetals as side products which would be formed under acidic conditions during the subsequent solvent switch from methanol to isopropanol. Subsequent solvent switch from methanol to isopropanol and crystallization gives compound of formula α-(4) in high purity without any or with minimum contamination with triethylammonium methanesulfonate salt.

Compound of Formula (6)

Compound of formula (6) is obtained by reduction of compound of formula α-(4) followed by a cyclization reaction. The resulting intermediate of the reduction of compound of formula α-(4) is compound of formula (5).

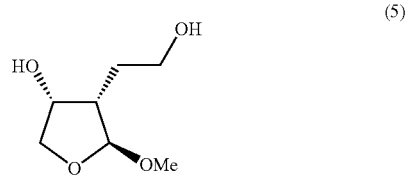
(5)

Compound of formula (5) is preferably not isolated but directly cyclized to compound of formula (6).

The reduction step can conveniently be accomplished by treatment of intermediate of formula α-(4) with metal hydrides such as lithium borohydride, sodium borohydride, sodium borohydride-lithium chloride in suitable anhydrous solvents.

Examples of suitable anhydrous solvents include but are not limited to dichloromethane, toluene, xylene, benzene, pentane, hexane, heptane, petrol ether, 1,4-thioxane, diethyl ether, diisopropyl ether, tetrahydrofuran, 1,4-dioxane, 1,2-dimethoxyethane, and in general any anhydrous solvent susceptible to being used in a chemical reduction process using the reduction agents cited above. A preferred solvent is tetrahydrofuran. According to a preferred embodiment, the reduction step is performed using lithium borohydride or sodium borohydride in tetrahydrofuran.

In case lithium borohydride is used as the reducing agent, the amount of reducing agent ranges between about 1 and about 1.5 equivalents based on the amount of compound of formula α-(4), preferably between about 1.1 and about 1.3 equivalents.

Said reduction step can be carried out at temperatures that range between about −78° C. and about 55° C., preferably between about −15° C. and about 45° C., and most preferably between about 0° C. and about 40° C. The reaction time may range up to about 24 hours, and suitably varies between about 2 and about 24 hours.

Compound of formula (5) may be converted to the desired compound of formula (6) by a cyclization reaction. The cyclization reaction occurs via an intramolecular transacetalisation and can be performed in any acid-compatible organic solvent or a combination of a water-miscible solvent and water and in the presence of a strong organic or inorganic acid. Said reaction is suitably performed by treatment of compound of formula (5) with a catalytic amount of a strong acid. In a preferred embodiment, the strong acid is selected from a group consisting of hydrochloric acid and sulfuric acid in tetrahydrofuran. Said cyclization step is preferably carried out at temperatures below about 5° C., more preferably below about −5° C.

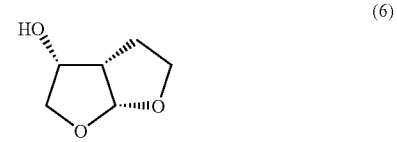
(6)

In a particularly preferred embodiment compound of formula (5), which upon reduction with lithium or sodium borohydride in tetrahydrofuran is obtained as a boron complex, is treated with a concentrated mineral acid and the decomplexation of compound of formula (5) and the cyclization of compound of formula (5) to compound of formula (6) are performed simultaneously. Preferably a strong mineral acid is used, more preferably concentrated sulfuric acid or concentrated hydrochloric acid, most preferably concentrated hydrochloric acid. The amount of hydrochloric acid may vary between 1.0 and 1.4 equivalents based on the applied amount of lithium or sodium borohydride, but is preferably between 1.1 and 1.3 equivalents.

With respect to the isolation of compound of formula (6) in pure form, it is desirable to remove the inorganic salts resulting from the reagents used in the reduction, decomplexation and cyclization steps. This may be done by an aqueous-organic solvent extraction procedure, but preferably this is done by adding a small excess of a base over the acid applied for the decomplexation of compound of formula (5) and cyclization reaction thereof to compound of formula (6). Subsequently, a solvent-switch from to a more apolar solvent is performed resulting in precipitation of the salts resulting from the reduction and decomplexation.

As a base used in the work-up of compound of formula (6) any base can be used as long as the solubility of its salt with the mineral acid used for the decomplexation and the cyclization reaction of compound of formula (5) to compound of formula (6) in the final solvent after the solvent-switch is low. For instance, if lithium borohydride in tetrahydrofuran is used in the reduction, concentrated aqueous HCl is used in the decomplexation/cyclization and ethyl acetate is the final solvent, then tertiary amines are suitable bases for the neutralization of the acid, particularly triethylamine. In that case, the boron salts and triethylamine hydrochloride almost fully precipitate and compound of formula (6) fully remains in solution. After filtration of the solids a solution of compound of formula (6) with high purity remains which can be processed to any desired form.

It is observed that the other enantiomer of compound of formula (6), namely compound of formula (6d), (3S,3aR,6aS) hexahydro-furo[2,3-b]furan-3-ol, is also an active moiety for HIV protease inhibitors.

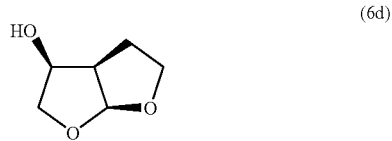

(6d)

As such, the identical methods, procedures, reagents and conditions, disclosed in the present invention, including the corresponding crystallization and epimerization, may be applied in the preparation of compound of formula (6d), by employing compounds of formula (1d), precursors thereof, and other intermediates in the preparation of compound of formula (6d), such as compounds of formula (4d) below.

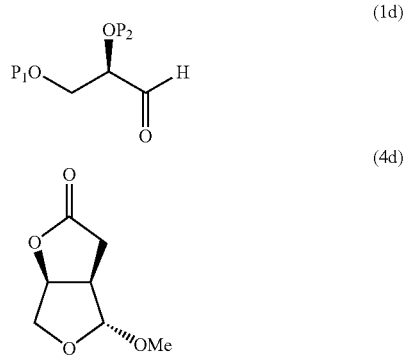

The compounds of formula (6) and (6d) find their particular use in the preparation of a medicament. According to a preferred embodiment, the present compounds of formula (6) and (6d) are used as precursors in the preparation of anti-viral drugs, in particular anti-HIV drugs, more in particular HIV protease inhibitors.

The compound of formula (6) and all intermediates leading to the formation of said stereoisomerically pure compound are of particular interest in preparing HIV protease inhibitors as disclosed in WO 95/24385, WO 99/65870, WO 00/47551, WO 00/76961 and U.S. Pat. No. 6,127,372, WO 01/25240, EP 0 715 618 and WO 99/67417 all incorporated herein by reference, and in particular, the following HIV-protease inhibitors.

[(1S,2R)-2-hydroxy-3-[[(4-methoxyphenyl)sulfonyl](2-methylpropyl)amino]-1-(phenyl-methyl)propyl]-carbamic acid (3R,3aS,6aR)-hexahydrofuro[2,3-b]furan-3-yl ester (HIV protease inhibitor 1);

[(1S,2R)-3-[[(4-aminophenyl)sulfonyl] (2-methylpropyl) amino]-2-hydroxy-1-(phenyl-methyl)propyl]-carbamic acid (3R,3aS,6aR)-hexahydrofuro[2,3-b]furan-3-yl ester (HIV protease inhibitor 2);

[(1S,2R)-3-[(1,3-benzodioxol-5-ylsulfonyl)(2-methylpropyl)amino]-2-hydroxy-1-(phenylmethyl)propyl]-carbamic acid (3R,3aS,6aR)-hexahydrofuro[2,3-b]furan-3-yl ester (HIV protease inhibitor 3), or any pharmaceutically acceptable addition salt thereof.

Thus, the present invention also relates to HIV protease inhibitors 1, 2, 3 or any pharmaceutically acceptable salt or prodrug thereof, obtained by using a compound of formula (6) prepared according to the present invention in the chemical synthesis of said HIV protease inhibitors. Such chemical synthesis is disclosed in the literature, for instance in WO 01/25240, EP 0 715 618 and WO 99/67417.

As such, the protease inhibitors referred above can be prepared utilizing the following general procedure. An N-protected amino epoxide of the formula

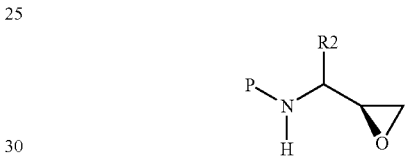

wherein P is an amino protecting group, and $R^2$ represents alkyl, aryl, cycloalkyl, cycloalkylalkyl and aralkyl radicals, which radicals are optionally substituted with a group selected from alkyl and halogen radicals, nitro, cyano, trifluoromethyl, $-OR^9$ and $-SR^9$, wherein $R^9$ represents hydrogen, alkyl, and halogen radicals; is prepared from the corresponding chloroketone in the presence of a base and a solvent system. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like.

Alternatively, a protected amino epoxide can be prepared starting with an L-amino acid which is reacted with a suitable amino-protecting group in a suitable solvent to produce an amino-protected L-amino acid ester of the formula:

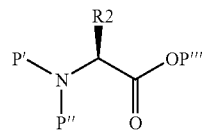

wherein P''' represents a carboxyl-protecting group, for example, methyl, ethyl, benzyl, tertiary-butyl and the like; $R^2$ is as defined above; and P' and P'' independently are selected from amine protecting groups, including but not limited to, arylalkyl, substituted arylalkyl, cycloalkenylalkyl and substituted cycloalkenylalkyl, allyl, substituted allyl, acyl, alkoxycarbonyl, aralkoxycarbonyl and silyl.

Additionally, the P' and/or P'' protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, for example, nitrophthalimidyl.

The amino-protected L-amino acid ester is then reduced, to the corresponding alcohol. For example, the amino-protected L-amino acid ester can be reduced with diisobutylaluminum hydride at −78° C. in a suitable solvent such as toluene. Preferred reducing agents include lithium aluminium hydride, lithium borohydride, sodium borohydride, borane, lithium tri-terbutoxyaluminum hydride, borane/THF complex. The resulting alcohol is then converted, for example, by way of a Swern oxidation, to the corresponding aldehyde of the formula:

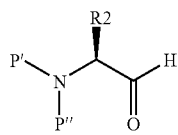

wherein P', P" and R² are as defined above. Thus, a dichloromethane solution of the alcohol is added to a cooled (−75° to −68° C.) solution of oxalyl chloride in dichloromethane and DMSO in dichloromethane and stirred for 35 minutes.

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydro thiaphene-S-oxide, toluenesulfonyl bromide and DMSO, trifluoro-methanesulfonyl anhydride (triflic anhydride) and DMSO, phosphorus pentachloride and DMSO, dimethylphosphoryl chloride and DMSO and isobutyl chloroformate and DMSO.

The aldehydes of this process can also be prepared by methods of reducing protected phenylalanine and phenylalanine analogs or their amide or ester derivatives by, for example, sodium amalgam with HCl in ethanol or lithium or sodium or potassium or calcium in ammonia. The reaction temperature may be from about −20° C. to about 45° C., and preferably from about 5° C. to about 25° C. Two additional methods of obtaining the nitrogen protected aldehyde include oxidation of the corresponding alcohol with bleach in the presence of a catalytic amount of 2,2,6,6-tetramethyl-1pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

The aldehyde resulting from the Swern oxidation is then reacted with a halomethyl-lithium reagent, which reagent is generated in situ by reacting an alkyllithium or arylithium compound with a dihalomethane represented by the formula X¹CH₂X² wherein X¹ and X² independently represent iodine, bromine or chlorine. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

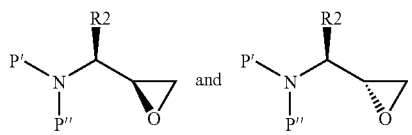

The diastereomers can be separated for example, by chromatography, or, alternatively, once reacted in subsequent steps the diastereomeric products can be separated. For compounds having the (S) stereochemistry, a D-amino acid can be utilized in place of the L-amino acid.

The addition of chloromethyllithium or bromomethyllithium to a chiral amino aldehyde is highly diastereoselective. Preferably, the chloromethyllithium or bromomethyllithium is generated in situ from the reaction of the dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent.

Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methyl-pyrrolidone are useful as solvents or as part of a solvent mixture. The reaction can be carried out under an inert atmosphere such as nitrogen or argon. For n-butyl lithium can be substituted other organometalic reagents reagents such as methyllithium, tertbutyl lithium, sec-butyl lithium, phenyllithium, phenyl sodium and the like. The reaction can be carried out at temperatures of between about −80° C. to 0° C. but preferably between about −80° C. to −20° C.

The conversion of the aldehydes into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromide, benzyl chloride or the like, in the presence of an organic or inorganic base. Alternatively, the protected aminosulfide alcohol can be alkylated with, for example, the alkylating agents above, to provide a sulfonium salts that are subsequently converted into the subject epoxides with tertamine or mineral bases.

The desired epoxides formed, using most preferred conditions, diastereoselectively in ratio amounts of at least about an 85:15 ratio (S:R). The product can be purified by chromatography to give the diastereomerically and enantiomerically pure product but it is more conveniently used directly without purification to prepare retroviral protease inhibitors. The foregoing process is applicable to mixtures of optical isomers as well as resolved compounds. If a particular optical isomer is desired, it can be selected by the choice of starting material, for example, L-phenylalanine, D-phenylalanine, L phenylalaminol, D-phenylalaminol, D-hexahydrophenylalaninol and the like, or resolution can occur at intermediate or final steps. Chiral auxiliaries such as one or two equivalents of camphor sulfonic acid, citric acid, camphoric acid, 2-methoxy-phenylacetic acid and the like can be used to form salts, esters or amides of the compounds of this invention. These compounds or derivatives can be crystallized or separated chromatographically using either a chiral or achiral column as is well known to those skilled in the art.

The amino epoxide is then reacted, in a suitable solvent system, with an equal amount, or preferably an excess of, a desired amine of the formula $R^3NH_2$, wherein $R^3$ is hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and di-substituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical.

The reaction can be conducted over a wide range of temperatures, for example, from about 10° C. to about 100° C., but is preferably, but not necessarily, conducted at a temperature at which the solvent begins to reflux.

Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzylamine, isobutylamine, n-butylamine, isopentylamine, isoamylamine, cyclohexanemethylamine, naphthylene methylamine and the like. The resulting product is a 3-(N-protected-amino)-3-($R^2$)-1-($NHR^3$)-propan-2-ol derivative, hereinafter referred to as an amino alcohol, and represented by the formulas:

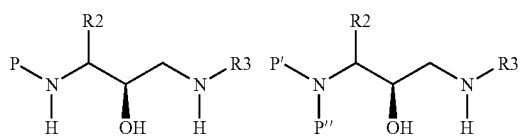

wherein P, P', P'', $R^2$ and $R^3$ are as described above. Alternatively, a haloalcohol can be utilized in place of the amino epoxide.

The amino alcohol defined above is then reacted in a suitable solvent with a sulfonyl chloride ($R^4SO_2Cl$) or sulfonyl anhydride in the presence of an acid scavenger. Suitable solvents in which the reaction can be conducted include methylene chloride, tetrahydrofuran. Suitable acid scavengers include triethylamine, pyridine. Preferred sulfonyl chlorides are methanesulfonyl chloride and benzenesulfonyl chloride. The resulting sulfonamide derivative can be represented, depending on the epoxide utilized by the formulas

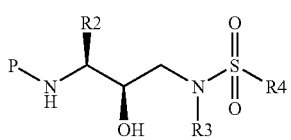

-continued

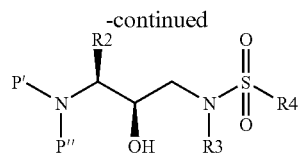

wherein P, P', P'', $R^2$, $R^3$ and $R^4$ are as defined above. These intermediates are useful for preparing protease inhibitor compounds and are also active inhibitors of retroviral proteases.

The sulfonyl halides of the formula $R^4SO_2X$ can be prepared by the reaction of a suitable Grignard or alkyl lithium reagent with sulfuryl chloride, or sulfur dioxide followed by oxidation with a halogen, preferably chlorine. Also, thiols may be oxidized to sulfonyl chlorides using chlorine in the presence of water under carefully controlled conditions. Additionally, sulfonic acids may be converted to sulfonyl halides using reagents such as $PCl_5$, and also to anhydrides using suitable dehydrating reagents. The sulfonic acids may in turn be prepared using procedures well known in the art. Such sulfonic acids are also commercially available. In place of the sulfonyl halides, sulfinyl halides ($R^4SOX$) or sulfenyl halides ($R^4SX$) can be utilized to prepare compounds wherein the $—SO_2—$ moiety is replaced by an $—SO—$ or $—S—$ moiety, respectively.

Following preparation of the sulfonamide derivative, the amino protecting group P or P' and P'' amino protecting groups are removed under conditions which will not affect the remaining portion of the molecule. These methods are well known in the art and include acid hydrolysis, hydrogenolysis and the like. A preferred method involves removal of the protecting group, for example, removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, for example, HCl or trifluoroacetic acid, in a suitable solvent system, for example, dioxane or methylene chloride. The resulting product is the amine salt derivative of the formula:

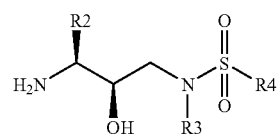

This amine can be coupled to a carboxylate represented by the formula

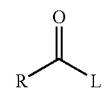

wherein R is the (3R,3aS,6aR) hexahydrofuro[2,3-b]furan-3-oxy group and L is an appropriate leaving group such as a halide. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethyl formamide, and the like, including mixtures thereof.

Alternatively the amine can be coupled to an activated (3R,3aS,6aR) hexahydro-furo[2,3-b]furan-3-ol succinimidyl carbonate. Activation of (3R,3aS,6aR) hexahydro-furo[2,3-b]furan-3-ol may be accomplished for instance by reaction with disuccinimidyl carbonate and triethylamine.

EXAMPLES

The following examples are meant to be illustrative of the present invention. These examples are presented to exemplify the invention and are not to be construed as limiting the invention's scope.

All reactions were performed under nitrogen atmosphere. Solvents and reagents were used as supplied without further purification. $^1$H NMR spectra were recorded at 200 MHz in CDCl$_3$ or DMSO-d$_6$ on a Bruker AC-200 NMR spectrometer. Quantitative $^1$H NMR was performed with chlorobenzene as the internal standard. All reported yields have been corrected for the impurity of the product.

The gas chromatography (GC) assay and e.e. determination of S-2,3-O-isopropylidene-glyceraldehyde in reaction mixtures was performed with an Agilent 6890 GC (EPC) and a Betadex column (part number 24305, Supelco or equivalent) of 60 m and with a film thickness of 0.25 µm using a column head pressure of 26.4 kPa, a column flow of 1.4 mL/min, a split flow of 37.5 mL/min and an injection temperature of 150° C. The used ramp was: initial temperature 60° C. (3 min), rate 5° C./min, intermediate temperature 130° C. (1 min), rate 25° C./min, final temperature 230° C. (8 min). Detection was performed with an FID detector at a temperature of 250° C. The retention times were as follows: chlorobenzene (internal standard) 13.9 min, S-2,3-O-isopropylidene-glyceraldehyde 15.9 min, R-2,3-O-isopropylidene-glyceraldehyde 16.2 min.

The GC assay and e.e. determination of R-3-(2,2-dimethyl-[1,3]dioxolan-4-yl)-acrylic acid ethyl ester was performed with above-described equipment but using an injection temperature of 250° C. The used ramp was: initial temperature 80° C. (1 min), rate 5° C./min, final temperature 225° C. (10 min). Detection was performed with a FID detector at a temperature of 250° C. The retention times were as follows: toluene 7.3 min, chlorobenzene (internal standard) 9.4 min, S-2,3-O-isopropylidene-glyceraldehyde 10.7 min, R-2,3-O-isopropylidene-glyceraldehyde 10.9 min, Z-3-(2,2-dimethyl-[1,3]dioxolan-4-yl)-acrylic acid ethyl ester 20.4 min, E-R-3-(2,2-dimethyl-[1,3]dioxolan-4-yl)-acrylic acid ethyl ester 22.6 min, E-S-3-(2,2-dimethyl-[1,3]dioxolan-4-yl)-acrylic acid ethyl ester 22.9 min, triethyl phosphonoacetate (TEPA) 25.5 min.

The GC assay for compounds α-(4) and β-(4) was performed with an Agilent 6890 GC (EPC) and a CP-Sil 5 CB column (part number CP7680 (Varian) or equivalent) of 25 m and with a film thickness of 5 µm using a column head pressure of 5.1 kPa, a split flow of 40 mL/min and an injection temperature of 250° C. The used ramp was: initial temperature 50° C. (5 min), rate 10° C./min, final temperature 250° C. (15 min). Detection was performed with an FID detector at a temperature of 250° C. The retention times were as follows: chlorobenzene (internal standard) 17.0 min, α-(4) 24.9 min, β-(4) 25.5 min.

Example 1

Preparation of S-2,3-O-isopropylidene-glyceraldehyde and conversion to R-3-(2,2-dimethyl-[1,3]dioxolan-4-yl)-acrylic acid ethylester To a well-stirred slurry of KIO$_4$ (530 g, 2.3 mol, 2.3 eq.), KHCO$_3$ (230 g, 2.3 mol, 2.3 eq.) in water (1200 g) was added dropwise a solution of L-5,6-O-isopropylidene-gulono-1,4-lactone (218.5 g, 1 mol) in water (135 g) and tetrahydrofuran (1145 g) during 3 h at 32-34° C. The reaction mixture was stirred for 4.5 h at 32° C. According to GC the oxidation was complete since the S-2,3-O-isopropylidene-glyceraldehyde content was 4.38 wt % and did not increase further. The reaction mixture was cooled to 5° C. and kept at this temperature for 14 h. The solids (mainly consisting of KIO$_3$) were removed by filtration and the cake was washed with tetrahydrofuran (115 mL) and with another portion of tetrahydrofuran (215 mL) by reslurrying. A sample was taken from the filtrate (2975 g) and analyzed by quantitative $^1$H NMR (DMSO-d$_6$) showing that the S-2,3-O-isopropylidene-glyceraldehyde content in the filtrate was 3.69 wt % corresponding to 109.6 g (0.843 mol) and a yield of 84% based on L-5,6-O-isopropylidene-gulono-1,4-lactone.

To 2953 g of the obtained filtrate (containing 108.8 g=0.837 mol S-2,3-O-isopropylidene-glyceraldehyde) at 13° C. was added dropwise under stirring triethyl phosphonoacetate (TEPA, 194.7 g, 97% pure, 0.843 mol, 1.01 eq.) during 25 min at 13-17° C. Subsequently, K$_2$CO$_3$ (838 g, 6.07 mol, 7.26 eq.) was added portionwise during 30 min at 17-25° C. The final pH of the reaction mixture was 11.6. The reaction mixture was stirred for another 17 h at 20° C. The aqueous and tetrahydro-furan phases were separated and the aqueous phase extracted twice with 660 mL of toluene. The combined tetrahydrofuran and toluene phases were concentrated in vacuo (260-25 mbar, temperature 28-56° C.) during 8 h giving 175.5 g of a light yellow liquid.

Quantitative $^1$H NMR indicated the presence of 78 wt % E-R-3-(2,2-dimethyl-[1,3]dioxolan-4-yl)-acrylic acid ethylester, 2.5 wt % Z-3-(2,2-dimethyl-[1,3]dioxolan-4-yl)-acrylic acid ethylester, 4.4 wt % TEPA (4.1 mole % of the initial amount) and 6.8 wt % toluene. This corresponds with a total R-3-(2,2-dimethyl-[1,3]dioxolan-4-yl)-acrylic acid ethylester yield of 141.2 g (0.706 mol) being 71% yield based on L-5,6-O-isopropylidene-gulono-1,4-lactone and 84% yield based on S-2,3-O-isopropylidene-glyceraldehyde. GC indicated that the e.e. of E-R-3-(2,2-dimethyl-[1,3]dioxolan-4-yl)-acrylic acid ethylester was >99%.

Example 2

Preparation of a mixture of compounds α-(4) and β-(4) from R-3-(2,2-dimethyl-[1,3]dioxolan-4-yl)-acrylic acid ethylester Using Various Types and Amounts of Bases without Isolation of the Nitro Addition Compound

Example 2A

Use of DBU in the Michael Addition and NaOMe as Additional Base in the Nef Reaction To R-3-(2,2-dimethyl-[1,3]dioxolan-4-yl)-acrylic acid ethylester (21.2 g oil, 94.5 wt % pure, 0.1 mol) was added nitromethane (13.0 g of a 51.7 wt % solution in methanol, 0.11 mol, 1.1 eq.) and the solution was cooled to 0° C. Subsequently, DBU (15.2 g, 0.1 mol, 1 eq.) was added dropwise during 25 min and the funnel was rinsed with methanol (1 g). The reaction mixture was heated up to 20° C. and stirred at that temperature for 17 h. The resulting solution (50 g) was divided in 2 equal parts; the other 25 g part was further processed as described in example 2B. The one 25 g part was cooled to 0° C. and NaOMe (10.0 g of a 29.6 wt % solution in methanol, 0.055 mol, 1.1 eq.) was added dropwise during 10 min at 0° C. and the funnel was rinsed with methanol (1.6 g). The reaction mixture was stirred for 50 min at 0° C. and then quenched into a solution of H$_2$SO$_4$ (17.9 g, 96 wt %, 0.175 mol, 3.5 eq.) in methanol (30.4 g) at 0-5° C. by dropwise addition during 60 min under vigorous stirring. The funnel was rinsed with methanol (2×4 g). The resulting reaction mixture was stirred for 2 h at 0° C. and subsequently quenched into a stirred mixture of saturated aqueous NaHCO$_3$ (300 mL) and ethyl acetate (100 mL) at 0-5° C. by dropwise addition during 15 min. The final pH was 6.9. Another portion of ethyl acetate (50 mL) was added and the pH was adjusted to 4.2 with H$_2$SO$_4$ (96 wt %). After phase separation the aqueous phase was extracted with ethyl acetate (1×150 mL, 3×100 mL). The combined organic phases were concentrated in vacuo at 40-50° C. giving 8.1 g of an orange solid. According to quantitative $^1$H NMR analysis this solid contained 4.2 g (0.026 mol) of compounds α-(4) and β-(4), corresponding to a total yield of 53% based on R-3-(2,2-dimethyl-[1,3]dioxolan-4-yl)-acrylic acid ethylester. The α-(4):β-(4) ratio was 3.1:1.

Example 2B

Use of DBU in the Michael Addition and No Additional Base in the Nef Reaction

The other 25 g solution as obtained after the Michael addition in example 2A was cooled to 0° C. and quenched into a solution of H$_2$SO$_4$ (7.8 g, 96 wt %, 0.076 mol, 1.5 eq.) in methanol (13.2 g) at 0° C. by dropwise addition during 40 min under vigorous stirring. The funnel was rinsed with methanol (7.7 g). The resulting reaction mixture was stirred for 4 h at 0° C. and subsequently worked up according to the procedure of example 2A giving a solid which, according to quantitative $^1$H NMR analysis, contained 2.8 g (0.0175 mol) of compounds α-(4) and β-(4), corresponding to a yield of 35% based on R-3-(2,2-dimethyl-[1,3]dioxolan-4-yl)-acrylic acid ethylester.

Example 2C

Use of TMG in the Michael Addition and NaOMe as Additional Base in the Nef Reaction To R-3-(2,2-dimethyl-[1,3]dioxolan-4-yl)-acrylic acid ethylester (47.5 g oil, 84.2 wt % pure, 0.2 mol) was added nitromethane (26.0 g of a 51.7 wt % solution in methanol, 0.22 mol, 1.1 eq.) and the solution was cooled to 0° C. Subsequently, TMG (23 g, 0.2 mol, 1 eq.) was added dropwise during 20 min and the funnel was rinsed with methanol (2 g). The reaction mixture was heated up to 20° C. and stirred at that temperature for 22 h. The solution was cooled to 0° C. and NaOMe (40.2 g of a 29.6 wt % solution in methanol, 0.22 mol, 1.1 eq.) was added dropwise during 15 min at 0° C. and the funnel was rinsed with methanol (6.4 g). After stirring for another 70 min at 0° C. the mixture was quenched into a solution of H$_2$SO$_4$ (71.6 g, 96 wt %, 0.7 mol, 3.5 eq.) in methanol (121.6 g) at 0-5° C. by dropwise addition during 70 min under vigorous stirring. The funnel was rinsed with methanol (2×15 g). The resulting reaction mixture was stirred for 145 min at 0° C. and subsequently quenched into a stirred mixture of saturated aqueous NaHCO$_3$ (1200 mL) and ethyl acetate (400 mL) at 0° C. by dropwise addition during 30 min. The final pH was 7.4. After adding an additional portion (200 mL) of ethyl acetate the pH was adjusted to 4.2 with H$_2$SO$_4$ (96 wt %). After phase separation the aqueous phase was extracted with ethyl acetate (4×400 mL). The combined organic phases were concentrated in vacuo at 40-50° C. giving 38.5 g of a yellow-orange solid which, according to quantitative $^1$H NMR analysis, contained α-(4) (12.2 g, 0.077 mol) and β-(4) (4.6 g, 0.029 mol) corresponding to a total yield of 53% based on R-3-(2,2-dimethyl-[1,3]dioxolan-4-yl)-acrylic acid ethylester and an α-(4):β-(4) ratio of 2.7:1.

Example 2D

Use of only NaOMe in the Michael Addition and in the Nef Reaction

To R-3-(2,2-dimethyl-[1,3]dioxolan-4-yl)-acrylic acid ethylester (47.5 g, 84.2 wt % pure, 0.2 mol) in methanol (200 g) was added nitromethane (26.0 g of a 51.7 wt % solution in methanol, 0.22 mol, 1.1 eq.) and the solution was cooled to 0° C. NaOMe (40 g of a 30 wt % solution in methanol, 0.22 mol, 1.1 eq.) was added and the reaction mixture was stirred for 18 h at 0° C. and then quenched into a solution of H$_2$SO$_4$ (58 g, 96 wt %, 0.57 mol, 2.9 eq.) in methanol (140 g) at −3-0° C. by dropwise addition during 75 min under vigorous stirring. The reaction mixture was stirred for 4 h at 0° C. and subsequently kept for 16 h at −30° C. According to quantitative $^1$H NMR analysis the total yield (in the reaction mixture) of α-(4) and β-(4) based on R-3-(2,2-dimethyl-[1,3]dioxolan-4-yl)-acrylic acid ethylester was 45% and the α-(4):β-(4) ratio 2.5:1. The reaction mixture was subsequently quenched into a stirred solution of NaHCO$_3$ (80 g) in water (1 L) at 0-5° C. by dropwise addition during 90 min. At the end of the quench a solution of NaHCO$_3$ (4 g) in water (50 mL) was added to adjust the pH to 5-5.5. After phase separation the aqueous solution was extracted with ethyl acetate (4×500 mL) and the combined organic phases were concentrated in vacuo at 30-40° C. giving 32 g of a red oil. According to quantitative $^1$H NMR analysis, this oil contained 13.2 g (0.084 mol) α-(4) and β-(4) corresponding to a total yield of 42% based on R-3-(2,2-dimethyl-[1,3]dioxolan-4-yl)-acrylic acid ethylester with the α-(4):β-(4) ratio being 3:1.

Example 3

Preparation of pure α-(4) from R-3-(2,2-dimethyl-[1,3]dioxolan-4-yl)-acrylic acid ethylester Using DBU in the Michael Addition, NaOMe as Additional Base in the Nef Reaction and Crystallization of α-(4) from Isopropanol Example 3A Using a Non-Improved Work-Up Procedure for α-(4) and β-(4)

To R-3-(2,2-dimethyl-[1,3]dioxolan-4-yl)-acrylic acid ethylester (42.3 g, 94.5 wt % pure, 0.2 mol) was added nitromethane (26.0 g of a 51.7 wt % solution in methanol, 0.22 mol, 1.1 eq.) and the solution was cooled to 0° C. Subsequently, DBU (30.4 g, 0.2 mol, 1 eq.) was added dropwise during 20 min and the funnel was rinsed with methanol (4 g). The reaction mixture was heated up to 20° C., stirred for another 16.5 h at this temperature and subsequently cooled to 0° C. Then, NaOMe (40.4 g of a 29.6 wt % solution in methanol, 0.22 mol, 1.1 eq.) was added dropwise during 20 min at 0° C. and the funnel was rinsed with methanol (6.4 g). The resulting solution was stirred for 50 min at 0° C. and then quenched into a solution of H$_2$SO$_4$ (71.6 g, 96 wt %, 0.7 mol, 3.5 eq.) in methanol (121.6 g) at 0-5° C. by dropwise addition during 70 min under vigorous stirring. The funnel was rinsed with methanol (2×16 g) and the reaction mixture was stirred for 2 h at 0-2° C. and then quenched into a stirred mixture of saturated aqueous NaHCO$_3$ solution (1.2 L) and ethyl acetate (400 mL) at 0-9° C. by dropwise addition during 17 min. The final pH was 7.2. The funnel was rinsed with methanol (40 ml) and the pH was adjusted to 4.0 with $H_2SO_4$ (96 wt %) at 9° C. After the addition of ethyl acetate (200 mL) and phase separation, the aqueous phase was extracted with ethyl acetate (600 mL, 3×400 mL). The combined organic phases were concentrated in vacuo at 40-50° C. giving 35.9 g of a yellow-orange semi-solid which, according to quantitative $^1$H NMR analysis, contained 16.5 g (0.104 mol) of α-(4) and β-(4) corresponding to a total yield of 52% based on R-3-(2,2-dimethyl-[1,3]dioxolan-4-yl)-acrylic acid ethylester. The α-(4):β-(4) ratio was 3.0:1.

The crude semi-solid product was dissolved in isopropanol (69.5 g) at 80° C. The resulting solution was cooled to 60° C., seeded and cooled further to 0° C. during 2 h which resulted in crystallization of α-(4). The solids were isolated by filtration, washed with isopropanol (30 mL, 20° C.) and dried on the air giving 12.0 g off-white crystalline product which, according to quantitative $^1$H NMR, consisted of 9.8 g α-(4) (31% yield based on R-3-(2,2-dimethyl-[1,3]dioxolan-4-yl)-acrylic acid ethylester) and 0.38 g β-(4) (1.2% yield based on R-3-(2,2-dimethyl-[1,3]dioxolan-4-yl)-acrylic acid ethylester). This corresponds to a crystallization yield of 60% (output α-(4)/[input α-(4)+β-(4)]) and an α-(4):β-(4) ratio of 26:1.

Example 3B

Using an Improved Work-Up Procedure for α-(4) and β-(4)

To R-3-(2,2-dimethyl-[1,3]dioxolan-4-yl)-acrylic acid ethylester (47.5 g, 84.2 wt % pure, 0.2 mol) was added nitromethane (26.0 g of a 51.7 wt % solution in methanol, 0.22 mol, 1.1 eq.) and the solution was cooled to 0° C. DBU (30.4 g, 0.2 mol, 1 eq.) was added dropwise during 30 min at 0-20° C. and the funnel was rinsed with methanol (4 g). The reaction mixture was heated up to 20° C., stirred for another 18 h at that temperature and cooled down to 0° C. Subsequently, NaOMe (40 g of a 29.6 wt % solution in methanol, 0.22 mol, 1.1 eq.) was added dropwise during 20 min at 0° C. and the resulting solution was stirred for 1 h at 0° C. Then, the mixture was quenched into a solution of $H_2SO_4$ (72 g, 96 wt %, 0.7 mol, 3.5 eq.) in methanol (72 g) at 0-5° C. by dropwise addition during 3 h under vigorous stirring. The reaction mixture was stirred for another 2 h at 0-5° C. and subsequently quenched into a stirred slurry of $KHCO_3$ (99 g) in water (200 mL) at 0-5° C. by dropwise addition during 1 h. The final pH was 4.1. After heating up to 20° C., the salts were removed by filtration and washed with ethyl acetate (500 mL). The aqueous mother liquor of the filtration (454 g) was concentrated in vacuo at 35° C. to remove the methanol until a final weight of 272 g and extracted with ethyl acetate (6×150 mL; first portions with the wash liquor of the salts filtration, then with fresh). The combined organic phases were concentrated in vacuo at 40-50° C. giving 40.4 g of a solid which, according to GC, contained 14.5 g α-(4) and 3.4 g β-(4) corresponding to a total yield of 57% based on R-3-(2,2-dimethyl-[1,3]dioxolan-4-yl)-acrylic acid ethylester and an α-(4):β-(4) ratio of 4.3:1.

The crude solid product was dissolved in ethyl acetate (300 mL) and the solution was washed with a mixture of saturated aqueous NaCl solution (25 mL) and water (10 mL). The organic layer which, according to GC, contained 14.1 g α-(4) and 3.4 g β-(4), was concentrated in vacuo to 42.4 g of a dreggy solid. To 38 g of this crude product was added isopropanol (62 g) and the solid was dissolved by heating to 60° C. The resulting solution was cooled to 50° C., seeded, and cooled further to 0° C. during 2 h which resulted in crystallization of α-(4). The solids were isolated by filtration, washed with isopropanol (2×20 mL, 0° C.) and dried on the air giving 12.9 g off-white crystalline product which, according to GC, contained 12.2 g α-(4). This corresponds to 39% yield based on R-3-(2,2-dimethyl-[1,3]dioxolan-4-yl)-acrylic acid ethylester) and a crystallization yield of 78% (output α-(4)/[input α-(4)+β-(4)]). No β-(4) could be detected.

Example 4

Preparation of pure α-(4) from R-3-(2,2-dimethyl-[1,3]dioxolan-4-yl)-acrylic acid ethylester by Crystallization of α-(4), Epimerization of β-(4) and Second Crystallization of α-(4)

To R-3-(2,2-dimethyl-[1,3]dioxolan-4-yl)-acrylic acid ethylester (42.3 g, 94.6 wt % pure, 0.2 mol) was added nitromethane (26.0 g of a 51.7 wt % solution in methanol, 0.22 mol, 1.1 eq.) and the solution was cooled to 0° C. Subsequently, DBU (30.4 g, 0.2 mol, 1 eq.) was added dropwise during 30 min at 0-20° C. and the reaction mixture was heated up to 20° C. and stirred for another 18 h at that temperature. The resulting reaction mixture was cooled to 0° C. and NaOMe (40 g of a 29.6 wt % solution in methanol, 0.22 mol, 1.1 eq.) was added dropwise at 0° C. The resulting solution was stirred for 1 h at 0° C. and quenched into a solution of $H_2SO_4$ (72 g, 96 wt %, 0.7 mol, 3.5 eq.) in methanol (72 g) at 0-5° C. by dropwise addition during 1½ h under vigorous stirring. The reaction mixture was stirred for 2 h at 0-5° C. and then quenched into a stirred slurry of $NaHCO_3$ (100 g), water (400 mL) and ethyl acetate (300 mL) at 0-5° C. by dropwise addition during 1 h. $NaHCO_3$ (40 g) was portionwise added to keep the pH above 3.5. The salts were removed by filtration at 0-5° C. and washed with ethyl acetate (300 mL). After phase separation the aqueous phase was extracted with ethyl acetate (300 mL of wash liquor, 3×150 mL fresh). The combined organic phases were concentrated in vacuo, ethyl acetate (200 mL) was added and the mixture concentrated in vacuo once more giving 33.2 g of a semi-solid which, according to quantitative $^1$H NMR analysis contained 13.5 g α-(4) and 4.0 g β-(4) corresponding to a total yield based on R-3-(2,2-dimethyl-[1,3]dioxolan-4-yl)-acrylic acid ethylester of 53% and an α-(4):β-(4) ratio of 3.5:1.

The crude product was dissolved in isopropanol (70 g) at 60° C. The resulting solution was cooled to 50° C., seeded and cooled further to 0° C. resulting in crystallization of α-(4) which was isolated by filtration, washed with cold (0° C.) isopropanol (2×15 mL) and dried on the air. This gave 12.3 g of α-(4) which, according to quantitative $^1$H NMR analysis, was 97.1 wt % pure and contained no β-(4). This corresponds to a (first crop) yield of 38% based on R-3-(2,2-dimethyl-[1,3]dioxolan-4-yl)-acrylic acid ethylester and a crystallization yield of 68% (output α-(4)/[input α-(4)+β-(4)]).

The combined mother and wash liquors of the first crystallization (108 g, containing 4.0 g β-(4) and 1.2 g α-(4)) were concentrated in vacuo to 17.9 g of a liquid. Subsequently, methanol (9.05 g) and $MeSO_3H$ (0.91 g, 0.29 eq.) were added and the mixture was heated up to reflux. After 2 h of reflux the epimerization reaction was complete (α-(4):β-(4) ratio>3). After cooling to 20° C., triethyl amine (0.96 g, 1 eq. based on $MeSO_3H$) was added and the mixture was concentrated in vacuo to 18.7 g of a viscous residue.

The residue was redissolved in isopropanol (13.9 g) at 50° C. After cooling to 45° C. the mixture was seeded and cooled down to 0° C. resulting in crystallization of α-(4) which was isolated by filtration, washed with cold (0° C.) isopropanol (2×6 mL) and dried on the air. This gave 2.24 g α-(4) which, according to quantitative $^1$H NMR analysis, was 95.3 wt % pure and contained no β-(4). This corresponds to a (second crop) yield of 6% based on R-3-(2,2-dimethyl-[1,3]dioxolan-4-yl)-acrylic acid ethylester and a crystallization yield of 43% (output α-(4)/[input α-(4)+β-(4)] after the epimerization). Thus, the total α-(4) yield (crop 1 and 2) based on R-3-(2,2-dimethyl-[1,3]dioxolan-4-yl)-acrylic acid ethylester was 44%.

Example 5

Crystallization of α-(4) Starting from Crude Mixtures of α-(4) and β-(4) from Other Solvents than Isopropanol

Example 5A

From tert-butanol

A crude mixture (6.5 g) of α-(4) and β-(4) as obtained in Example 2A (containing 3.37 g of α-(4)+β-(4) in a ratio of 3.1:1) was dissolved in tert-butanol (16 g) at 72° C. Cooling to 55° C., seeding and further cooling to 25° C. resulted in the crystallization of a-(4) which was isolated by filtration, washed with isopropanol (5 mL, 20° C.) and dried in vacuo. This gave α-(4) (1.85 g) which, according to quantitative $^1$H NMR analysis, consisted of 82.9 wt % pure α-(4) corresponding to a crystallization yield of 46% ([output α-(4)+β-(4)]/[input α-(4)+β-(4)]) with an α-(4):β-(4) ratio of 30:1.

Example 5B

From tert-amylalcohol

A crude mixture (7.25 g) of α-(4) and β-(4) (containing 3.44 g of α-(4)+β-(4) in a ratio of 2.9:1) was dissolved in tert-amylalcohol (15.7 g) at 70° C. Cooling to 60° C., seeding and further cooling to 40° C. did not result in crystallization. After seeding once more at 40° C. the solution was further cooled and crystallization of α-(4) started at 27° C. The mixture was further cooled down to 2° C. and the crystals of α-(4) were isolated by filtration, washed with tert-amylalcohol (7.5 mL, 20° C.) and dried in vacuo. This gave 2.35 g of an off-white product which, according to quantitative $^1$H NMR analysis, consisted of 1.91 g α-(4) and 0.11 g β-(4) corresponding to a crystallization yield of 59% ([output α-(4)+β-(4)]/[input α-(4)+β-(4)]) and an α-(4):β-(4) ratio of 18:1.

Example 6

Crystallization of Pure α-(4) from a Mixture of α-(4) and β-(4) with Simultaneous Epimerization of β-(4)

A solution of light-brown α-(4) (5.0 g, 96.6 wt % pure, 30.6 mmol, containing no β-(4)) and MeSO$_3$H (0.3 g, 0.1 eq.) in methanol (200 mL) was stirred at 20° C. for 92 h resulting in epimerization to an α-(4):β-(4) ratio of 3.6:1. The reaction mixture was subsequently concentrated in vacuo (20 mbar; 45° C.) to give 5.2 g of a sticky solid. This was taken up in methanol (50 mL) and concentrated once more in vacuo (20 mbar; 50° C.) to give 5.1 g of a dry light-brown solid which, according to quantitative $^1$H NMR analysis, contained α-(4) in 90 wt % purity (4.6 g, 29 mmol). No β-(4) was detected. Thus, nearly all (96%) initial α-(4) had been recovered.

Example 7

Preparation of pure α-(4) from freshly prepared S-2,3-O-isopropylidene-glyceraldehyde Using an Improved Procedure and Crystallization of α-(4), Epimerization of β-(4) and a Second Crystallization of α-(4)

To 175 g of the E-R-3-(2,2-dimethyl-[1,3]dioxolan-4-yl)-acrylic acid ethylester as prepared in Example 1 (78 wt % pure, 136.5 g, 0.68 mol) was added nitromethane (88.6 g of a 51.7 wt % solution in methanol, 0.75 mol, 1.1 eq.) and the solution was cooled to 10° C. Subsequently, DBU (103.4 g, 0.68 mol, 1 eq.) was added dropwise during 35 min at 10-21° C. and the funnel was rinsed with methanol (7 g). After stirring for 18 h at 20° C. the resulting dark-red solution was cooled to 0° C. and NaOMe (134.6 g of a 30 wt % solution in methanol, 0.748 mol, 1.1 eq.) was added dropwise during 35 min at 0° C. and the funnel was rinsed with methanol (10 g). After 30 min stirring at 0° C. the reaction mixture was quenched into a solution of H$_2$SO$_4$ (243 g, 96 wt %, 2.38 mol, 3.5 eq.) in methanol (243 g) at 0-5° C. by dropwise addition during 3 h under vigorous stirring and the funnel was rinsed with methanol (2×15 g). After 2 h stirring at 0-2° C. the reaction mixture was quenched into a stirred slurry of KHCO$_3$ (353 g) in water (680 mL) at 0-6° C. by dropwise addition during 1 h. The pH was 7 at the end of the quench and was adjusted to 4.1 with H$_2$SO$_4$ (96 wt %) at 0° C. After heating up to 20° C. the salts were removed by filtration and washed with ethyl acetate (3×375 mL). The wash liquor was used later on in the extractions. The mother liquor of the filtration (1380 g), according to GC, contained 3.08 wt % α-(4) and 0.82 wt % β-(4) (corresponding to a total yield of 50% based on E-R-3-(2,2-dimethyl-[1,3]dioxolan-4-yl)-acrylic acid ethylester and an α-(4):β-(4) ratio of 3.75:1) was concentrated in vacuo to remove the methanol. To the resulting residue (760 g) water (80 g) was added and the pH was adjusted to 4.1 with H$_2$SO$_4$ (96 wt %). The resulting aqueous solution was extracted with ethyl acetate (700 mL, 4×500 mL). The combined organic phases were concentrated in vacuo at 35-40° C. to 181 g of a residue. The volatiles were coevaporated 3× with isopropanol (2×140 g and 90 g) giving a residue (146 g) consisting of a crude mixture of α-(4) and β-(4).

The crude mixture (146 g) was dissolved in isopropanol (202 g) at 70° C. Insoluble material was removed by filtration and washed with isopropanol (5 mL); the weight after drying was 0.33 g. The filtrate (346 g) was cooled to 50° C. resulting in spontaneous crystallization of α-(4). The slurry was further cooled to 1° C. during 4 h and the crystals were isolated by filtration, washed with isopropanol (2×100 mL, 0° C.) and dried in vacuo for 17 h at 35° C. giving an off-white crystalline product (44.2 g). According to quantitative GC it consisted of 89.0 wt % α-(4) and 1.0 wt % β-(4) corresponding to a total yield of 37% based on E-R-3-(2,2-dimethyl-[1,3]dioxolan-4-yl)-acrylic acid ethylester and an α-(4):β-(4) ratio of 89:1.

The mother liquor and wash liquors of the first α-(4) crystallization (totally 374 g) were concentrated in vacuo to 90.8 g, methanol (120 mL) was added and the resulting mixture concentrated to 83 g. Methanol (120 mL) was added once more and the mixture concentrated to 83 g. To the residue was added methanol (45 g) and MeSO$_3$H (2.66 g, 0.0277 mol, 0.2 eq. based on total α-(4)+β-(4) present in the mother liquor and wash liquors) and the solution was heated up to reflux. After 1 h at reflux (60-65° C.) GC indicated that the epimerization was complete (the α-(4):β-(4) ratio was 3.1:1) and the solution was cooled to 33° C., neutralized with triethyl amine (2.94 g, 1.05 eq. based on MeSO₃H) and concentrated in vacuo. To the resulting residue was added isopropanol (120 mL) and the mixture was concentrated in vacuo to give 88 g of a residue.

The residue was dissolved in isopropanol (37 g) at 47° C. The resulting solution was cooled down to 2° C. during 2.5 h; crystallization started spontaneously at 30° C. The crystalline product was isolated by filtration, washed with isopropanol (3×20 mL, 0° C.) and dried in vacuo (17 h at 35° C.) to give 10.1 g of a white crystalline product which according to GC consisted of 96.4 wt % α-(4) and 0.065 wt % β-(4), corresponding with a total yield based on E-R-3-(2,2-dimethyl-[1,3]dioxolan-4-yl)-acrylic acid ethylester of 9% and an α-(4):β-(4) ratio of >1000:1.

Thus, the total yield of the first and second crop of α-(4) based on E-R-3-(2,2-dimethyl-[1,3]dioxolan-4-yl)-acrylic acid ethylester was 46%.

Example 8

Preparation of pure (3R,3aS,6aR) hexahydro-furo[2,3-b]furan-3-ol from α-(4) intermediate The procedure described in WO03/022853, Example IV, last step, was followed.

Example 9

Preparation of pure α-(4) from R-3-(2,2-dimethyl-[1,3]dioxolan-4-yl)-acrylic acid ethylester by Direct Crystallization of α-(4) from a Crude Mixture of β-(4) and α-(4) and Simultaneous Epimerization of β-(4) to α-(4)

To R-3-(2,2-dimethyl-[1,3]dioxolan-4-yl)-acrylic acid ethylester (399.5 g, 75.1 wt % pure, 1.5 mol) was added nitromethane (915.0 g of a 11 wt % solution in methanol, 1.65 mol, 1.1 eq.) and the solution was cooled to 0° C. Subsequently, DBU (233.3 g, 1.5 mol, 1 eq.) was added dropwise during 50 min at 0-5° C. and the reaction mixture was heated up to 20° C. and stirred for another 16 h at that temperature. The resulting reaction mixture was cooled to 0° C. and NaOMe (594.0 g of a 15 wt % solution in methanol, 1.65 mol, 1.1 eq.) was added dropwise during 50 min at 0° C. The resulting solution was stirred for 1 h at 0° C. and quenched into a solution of H₂SO₄ (368 g, 96 wt %, 3.6 mol, 2.4 eq.) in methanol (370 g) at 0-5° C. by dropwise addition during 3 h under vigorous stirring. The reaction mixture was stirred for 2 h at 0-5° C. and then quenched into a stirred slurry of KHCO₃ (457.6 g), in water (870 mL) at 0-5° C. by dropwise addition during 1 h. KHCO₃ was portionwise added to keep the pH above 3.5. The formed salts were removed by filtration at 0-5° C. and washed with methanol (530 mL). After concentration in vacuo of the combined filtrate and washing to approximately 1000 ml the aqueous phase was extracted with toluene (2×2100 mL, 3×1050 mL). The combined organic phases were concentrated in vacuo, giving 202.9 g of a semi-solid.

Subsequently, methanol (42.6 g) and MeSO₃H (6.06 g, 0.04 eq.) were added and the mixture was heated up to 50° C. After 2 h of stirring at this temperature the mixture was cooled to 20° C. and stirring was continued for an additional 12 h. After cooling to −5° C., triethyl amine (6.60 g, 1.1 eq. based on MeSO₃H) was added and the mixture was stirred for another 2 h. The crystalline α-(4) which was isolated by filtration, washed with cold (−5° C.) isopropanol (3×70 mL) and dried on the air. This gave 120.0 g α-(4) which, according to quantitative GC analysis, was 99.0 wt % pure and contained 0.09 area % of β-(4). This corresponds to a yield of 51% based on R-3-(2,2-dimethyl-[1,3]dioxolan-4-yl)-acrylic acid ethylester.

The invention claimed is:

1. A method for the synthesis of (3R,3aS,6aR) hexahydro-furo[2,3-b]furan-3-ol having the structure of formula (6),

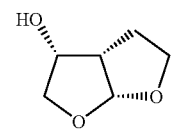

which method comprises the step of reducing the intermediate of formula α-(4):

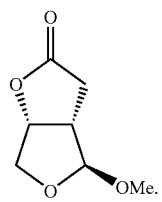

2. A method according to claim 1 which method further comprises crystallizing intermediate of formula α-(4) with a solvent prior to the reduction thereof.

3. A method according to claim 1 which method further comprises
a) epimerizing with acid intermediate of formula β-(4) into the intermediate of formula α-(4); and

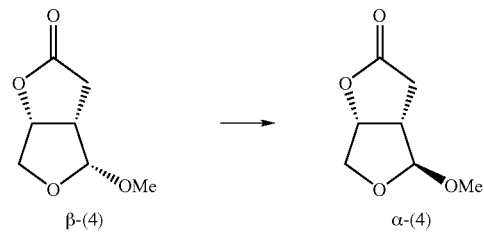

b) crystallizing intermediate of formula α-(4) with a solvent prior to the reduction thereof.

4. A method according to claim 3 which method further comprises after crystallizing intermediate of formula α-(4),
a) epimerizing with acid intermediate of formula β-(4) in the mother liquor of said crystallization into the intermediate of formula α-(4); and

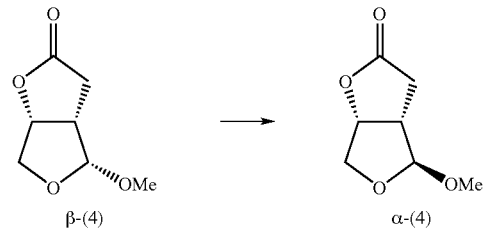

b) crystallizing intermediate of formula α-(4) with a solvent; prior to the reduction thereof.

5. A method according to claim 3 wherein the epimerization of compound of formula β-(4) to compound of formula α-(4) and crystallization of compound of formula α-(4) occur simultaneously.

6. A method according to claim 5, wherein the simultaneous epimerization of compound of formula β-(4) to compound of formula α-(4) and the crystallization of compound of formula α-(4) is performed in methanol in the presence of an acid by evaporation or partial evaporation of the methanol.

7. A method according to claim 1 which method comprises the steps of:
   a) treating compound of formula (3) with a base and subsequently with an acid in the presence of a non-methanolic solvent; and subsequently reacting with methanol under acidic conditions;

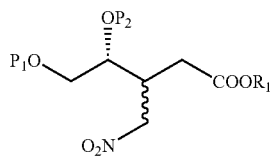

(3)

wherein
P$^1$ and P$^2$ are each independently a hydrogen, a hydroxy-protecting group or may together form a vicinal-diol protecting group,
R$^1$ is alkyl, aryl or aralkyl;
resulting in intermediates of formula (4); and

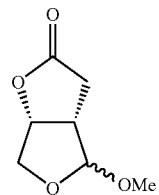

(4)

b) reducing intermediate of formula (4) with a reducing agent and applying an intramolecular cyclization reaction to obtain compound of formula (6)

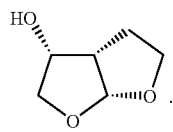

(6)

8. A method according to claim 7 wherein compounds of formula (3) are obtained by reacting compounds of formula (2) with nitromethane and a base

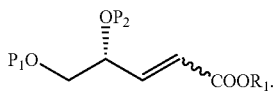

(2)

9. A method according to claim 8 wherein compounds of formula (2) are obtained by condensing an intermediate of formula (1) or its hydrate, hemihydrate or a mixture thereof with phosphonates of the formula (R$^6$O)$_2$P(=O)—CH$_2$—C(=O)OR$^1$, wherein
P$^1$ and P$^2$ are as defined in claim 1,
R$^1$ is as defined in claim 1,
R$^6$ is alkyl, aryl or aralkyl,

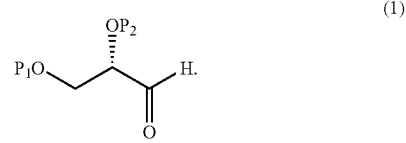

(1)

10. A method according to claim 7 wherein P$^1$ and P$^2$ together form a dialkyl methylene radical.

11. A method according to claim 8 wherein the base employed for the conversion of compounds of formula (2) into compounds of formula (3) is DBU or TMG or derivatives thereof.

12. A method according to claim 9 wherein the phosphonate of the formula (R$^6$O)$_2$P(=O)—CH$_2$—C(=O)OR$^1$ is triethyl phosphonoacetate (TEPA).

13. A method according to claim 7 wherein the conversion of compounds of formula (3) into compounds of formula (4) is performed with a base selected from the group of sodium methoxide, lithium methoxide, DBU or TMG or mixtures thereof.

14. A method according to claim 8, wherein the conversion of compounds of formula (2) into compounds of formula (4) is performed by using DBU or TMG as the base in the conversion of compounds of formula (2) to compounds of formula (3), not isolating compounds of formula (3) and using sodium or lithium methoxide as additional base in the conversion of compounds of formula (3) to compounds of formula (4).

15. A method according to claim 7 wherein the acid employed in the conversion of compounds of formula (3) into compounds of formula (4) is concentrated sulphuric acid in an amount of 2.5 to 5 equivalents based on compound of formula (2) as a 20 to 80 wt % solution in methanol.

16. A method according to claim 2 wherein crystallization of compound of formula α-(4) is performed in an alcohol.

17. A method according to claim 16 wherein the alcohol is isopropanol, t-amyl alcohol or t-butanol.

18. A method for the conversion of compound of formula β-(4) into the compound of formula α-(4) which comprises an epimerization with acid

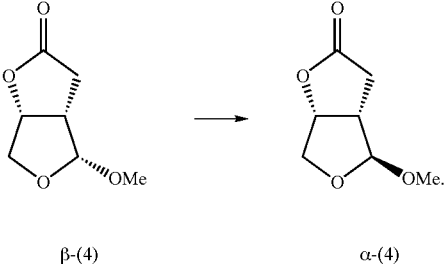

β-(4)    α-(4)

19. A method according to claim 3 wherein epimerization of compound of formula β-(4) into compound of formula α-(4) is performed with 0.05 to 1.5 equivalents of MeSO$_3$H in methanol.

20. A method according to claim 3 wherein the epimerization is performed at a temperature between 40° C. and reflux temperature.

* * * * *